United States Patent [19]

Bryant et al.

[11] Patent Number: 5,057,221

[45] Date of Patent: * Oct. 15, 1991

[54] AEROBIC BIOLOGICAL DEHALOGENATION REACTOR

[75] Inventors: Curtis W. Bryant, Tucson, Ariz.; William A. Barkley, Maple Valley, Wash.

[73] Assignee: Weyerhaeuser Company, Tacoma, Wash.

[*] Notice: The portion of the term of this patent subsequent to Aug. 6, 2008 has been disclaimed.

[21] Appl. No.: 287,477

[22] Filed: Dec. 19, 1988

[51] Int. Cl.$^5$ .............................................. C02F 3/34
[52] U.S. Cl. .................................. 210/610; 210/617; 210/631; 210/747; 210/908; 435/250; 435/267
[58] Field of Search ........ 210/603, 610, 611, 614–617, 210/620, 630, 631, 747, 908, 909, 928; 435/247–250, 267, 281, 858

[56] References Cited

U.S. PATENT DOCUMENTS

| | | | |
|---|---|---|---|
| 3,979,283 | 9/1976 | Prudom | 210/11 |
| 4,266,034 | 5/1981 | Patel et al. | 435/253 |
| 4,323,649 | 4/1982 | Higgins | 435/136 |
| 4,344,848 | 8/1982 | Hakulinen | 210/611 X |
| 4,385,121 | 5/1983 | Knowlton | 435/244 |
| 4,401,569 | 8/1983 | Jhaveri et al. | 210/610 |
| 4,447,541 | 5/1984 | Peterson | 435/264 |
| 4,452,894 | 6/1984 | Olsen et al. | 435/253 |
| 4,455,373 | 6/1984 | Higgins | 435/132 |
| 4,473,643 | 9/1984 | Higgins | 435/157 |
| 4,493,895 | 1/1985 | Colaruotolo et al. | 210/610 X |
| 4,623,464 | 11/1986 | Ying et al. | 210/616 |
| 4,664,805 | 5/1987 | Focht | 210/611 |
| 4,713,340 | 12/1987 | Crawford | 435/253 |
| 4,713,343 | 12/1987 | Wilson, Jr. et al. | 435/264 |
| 4,749,491 | 6/1988 | Lawes et al. | 210/610 |
| 4,765,901 | 8/1988 | Field | 210/603 |

FOREIGN PATENT DOCUMENTS

| | | |
|---|---|---|
| 1148488 | 6/1983 | Canada . |
| 3208977A1 | 9/1983 | Fed. Rep. of Germany . |
| 239197A1 | 9/1986 | Fed. Rep. of Germany . |

OTHER PUBLICATIONS

Bouwer and McCarty, "Transformations of 1- and 2-Carbon Halogenated Aliphatic Organic Compounds Under Methanogenic Conditions," *Appl. Environ. Microbiol.* 45:1286–1294 (1983).

Alexander, "Biodegradation of Organic Chemicals," *Environ. Sci. Technol.* 18:106–111 (1985).

Patterson and Kodukala, "Biodegradation of Hazardous Organic Pollutants," *CEP*, Apr., 1981, pp. 48–55.

McDougall et al., "Contaminant and Treatment of the Love Canal Landfill Leachate," *Jour. W.P.C.F.* 52:2914–2924 (1980).

Schmidt et al., "Degradation of Chlorophenols by a Defined Mixed Microbial Community," *Appl. Environ. Microbiol.* 45:1038–1044 (1983).

(List continued on next page.)

*Primary Examiner*—Tom Wyse
*Attorney, Agent, or Firm*—Klarquist, Sparkman, Campbell, Leigh & Whinston

[57] ABSTRACT

Methylotrophic and heterotrophic microorganisms are supported on a rigid substrate bed. Oxygen, such as from air, and a low-molecular-weight alkane, such as methane, flow through the bed. Organic compounds in contaminated water processing through the bed are biodegraded by the microorganisms. The bed may be formed of manufactured particulate material, such as of activated carbon. These bed-forming materials may be preloaded with organic carbon materials to provide a nutrient source for the microoganisms. The biological reactor may continuously treat effluent from, for example, an industrial plant, in either a batch or continuous process. A water solids removal subsystem may be positioned upstream of the biological reactor to remove organic carbon compounds and various solids from the contaminated water prior to treatment. Optional bed cleaning mechanisms may also be included in the biological reactor. A methane gas source for the biological reactor may comprise a methanogenic microorganism-containing second reactor which uses liquid from the first biological reactor as a carbon and energy source.

23 Claims, 7 Drawing Sheets

OTHER PUBLICATIONS

Marinucci and Bartha, "Biodegradation of 1,2,3- and 1,2,4-Trichlorobenzene in Soil and in Liquid Enrichment Culture," *App. Environ. Microbiol.* 38:811–817 (1979).

Healy and Young, "Catechol and Phenol Degradation by a Methanogenic Population of Bacteria," *App. Environ. Microbiol.* 35:216–218 (1978).

Klecka and Maier, "Kinetics of Microbial Growth on Pentachlorophenol," *App. Environ. Microbiol.* 48:46–53 (1985).

Gibson and Suflita, "Extrapolation of Biodegradation Results to Groundwater Aquifers: Reductive Dehalogenation of Aromatic Compounds," *App. Environ. Microbiol.* 52:681–688 (1986).

Zeyer et al., "Rapid Microbial Mineralization of Toluene and 1,3-Dimethylbenzene in the Absence of Molecular Oxygen," *App. Environ. Microbiol.* 52:944–947 (1986).

Mikesell and Boyd, "Complete Reductive Dechlorination and Mineralization of Pentachlorophenol by Anaerobic Microorganisms," *App. Environ. Microbiol.* 52:861–865 (1986).

Dalton, H., and Stirling, D. I., "Co-Metabolism," *Phil. Trans., R. Soc. Lond.,* B 297:481–496 (1982).

Wilson, J. T., and Wilson, B. H., "Biotransformation of Trichloroethylene in Soil," *Applied and Environ. Microbiol.* 48:242–243 (Jan. 1985).

Fogel, M. M., Taddeo, A. R., and Fogel, S., "Biodegradation of Chlorinated Ethenes by a Methane-Utilizing Mixed Culture," *Applied and Environ. Microbiol.* 51:720–724 (Apr. 1986).

Higgins, I. J., Best, D. J., and Hammond, R. C., "New Findings in Methane-Utilizing Bacteria Highlight Their Importance in the Biosphere and Their Commercial Potential," *Nature* 286:561–564 (Aug. 1980).

Strand, S. E. and Shippert, L., "Oxidation of Chloroform in an Aerobic Soil Exposed to Natural Gas," *Applied and Environ. Microbiol.* 52:203–205 (Jul. 1986).

Haber, C. L., et al., "Methylotrophic Bacteria: Biochemical Diversity and Genetics," *Science* 221:1147–1153 (Sep. 1983).

Best, D. J. and Higgins, I. J., "Methane-Oxidizing Activity and Membrane Morphology in a Methanol-Grown Obligate Methanotroph, *Methylosinus trichosporium* OB3b," *J. Gen. Microbiol.* 125:73–84 (1981).

Scott, D., Brannan, J. and Higgins, I. J., "The Effect of Growth Conditions on Intracytoplasmic Membranes and Methane Monooxygenase Activities in *Methylosinus trichosporium* OB3b," *J. Gen. Microbiol.* 125:63–72 (1981).

Dostalek, M. and Molin, N., "Studies of Biomass Production of Methanol Oxidizing Bacteria," in *Single-Cell Protein II* (Tannenbaum, S. R. and Wang, D. C., eds.), MIT Press, pp. 385–401.

Coty, V. F., "A Critical Review of the Utilization of Methane," *Biotech. and Bioeng. Symposium No. 1* (Second International Conference on Global Impacts of Applied Microbiology, Addis Ababa, Ethiopia, 1967), Interscience, 1969, pp. 105–117.

Little, C. D., et al., "Trichloroethylene Biodegradation by a Methane-Oxidizing Bacterium," *Applied and Environ. Microbiol.* 54:951–956 (Apr. 1988).

Hanson, R. S., "Ecology and Diversity of Methylotrophic Organisms," *Advances in Applied Microbiology*, vol. 26:3–39 (1980) Academic Press.

Colby, J., Dalton, H. and Whittenbury, R., "Biological and Biochemical Aspects of Microbial Growth on $C_1$ Compounds," *Ann. Rev. Microbiol.* 33:481–517 (1979).

Higgins, I. J., et al., "Methane-Oxidizing Microorganisms," *Microbiol. Reviews* 45:556–590 (Dec. 1981).

Nichols, P. D., et al., "Detection of a Microbial Consortium, Including Type II Methanotrophs, by Use of Phospholipid Fatty Acids in an Aerobic Halogenated Hydrocarbon-Degrading Soil Column Enriched with Natural Gas," *Environ. Toxicol. and Chem.* 6:89–97 (1987).

Whittenbury, R. and Dalton, H., "The Methylotrophic Bacteria," in *The Prokaryotes*, vol. I, Ch. 71, pp. 894–902 (1981).

Leadbetter, E. R. and Foster, J. W., "Studies on Some Methane-Utilizing Bacteria," *Archiv fur Mikrobiologie* Bd. 30:91–118 (1958).

Higgins, I. J. and Quayle, J. R., "Oxygenation of Methane by Methane-Grown *Pseudomonas methanica* and *Methanomonas methanooxidans*," *Biochem. J.* 118:201–208 (1970).

Hou, C. T., et al., "Microbial Oxidation of Gaseous Hydrocarbons: Epoxidation of $C_2$ to $C_4$ n-Alkenes by Methylotrophic Bacteria," *Applied and Environ. Microbiol.* 38:127–134 (Jul. 1979).

(List continued on next page.)

OTHER PUBLICATIONS

Vogel, T. M. and McCarty, P. L., "Biotransformation of Tetrachloroethylene to Trichloroethylene, Dichloroethylene, Vinyl Chloride, and Carbon Dioxide under Methanogenic Conditions," *Applied and Environ. Microbiol.* 49:1080–1083 (May 1985).

Bouwer, E. J. and McCarty, P. L., "Utilization Rates of Trace Halogenated Organic Compounds in Acetate--Grown Biofilms," *Biotech. and Bioeng.* 27:1564–1571 (1985).

Steiert, J. G., Pignatello, J. J. and Crawford, R. L., "Degradation of Chlorinated Phenols by a Pentachlorophenol-Degrading Bacterium," *Applied and Environ. Microbiol.* 53:907–910 (May 1987).

Steiert, J. G. and Crawford, R. L., "Catabolism of Pentachlorophenol by a Flavobacterium Sp.," *Biochem. Biiophys. Res. Comm.* 141:825–830 (Dec. 1986).

Saber, D. L. and Crawford, R. L., "Isolation and Characterization of Flavobacterium Strains that Degrade Pentachlorophenol," *Applied and Environ. Microbiol.* 50:1512–1518 (Dec. 1985).

Crawford, R. L. and Mohn, W. W., "Microbiological Removal of Pentachlorophenol from Soil Using a Flavobacterium," *Enzyme Microb. Technol.* 7:617–620 (Dec. 1985).

Apajalahti, J. H. A. and Salkinoja-Salonen, M. S., "Dechlorination and para-Hydroxylation of Polychlorinated Phenols by Rhodococcus chlorophenolicus," *J. Bacteriol.* 169:675–681 (Feb. 1987).

Apajalahti, J. H. A. and Salkinoja-Salonen, M. S., "Degradation of Polychlorinated Phenols by Rhodococcus chlorophenolicus," *Applied Microbiol. Biotechnol.* 25:62–67 (1986).

Janssen, D. B., et al., "Degradation of Halogenated Aliphatic Compounds by Xanthobacter autotrophicus GJ10," *Applied and Environ. Microbiol.* 49:673–677 (Mar. 1985).

Nelson, M. J. K., et al., "Aerobic Metabolism of Trichloroethylene by a Bacterial Isolate," *Applied and Environ. Microbiol.* 52:383–384 (Aug. 1986).

Nelson, M. J. K., et al., "Biodegradation of Trichloroethylene and Involvement of an Aromatic Biodegradative Pathway," *Applied and Environ. Microbiol.* 53:949–954 (May 1987).

DeBont J. A. M., et al., "Microbial Degradation of 1,3-Dichlorobenzene," *Applied and Environ. Microbiol.* 52:677–680 (Oct. 1986).

Schraa, G., et al., "Degradation of 1,4-Dichlorobenzene by Alcaligenes sp. Strain A175," *Applied and Environ. Microbiol.* 52:1374–1381 (Dec. 1986).

Kilbane, J. J., et al., "Biodegradation of 2,4,5-Trichlorophenoxyacetic Acid by a Pure Culture of Pseudomonas cepacia," *Applied and Environ. Microbiol.* 44:72–78 (Jul. 1982).

Karns, J. S., et al., "Metabolism of Halophenols by 2,4,5-Trichlorophenoxyacetic Acid-Degrading Pseudomonas cepacia," *Applied and Environ. Microbiol.* 46:1176–1181 (Nov. 1983).

Reineke, W. and Knackmuss, H.-J. "Microbial Metabolism of Haloaromatics: Isolation and Properties of a Chlorobenzene-Degrading Bacterium," *Applied and Environ. Microbiol.* 47:395–402 (Feb. 1984).

Pain, S., "Microbes 'Could Break Down Dioxin'," *New Scientist*, p. 36 (Feb. 25, 1988).

Chu, J. P. and Kirsch, E. J., "Metabolism of Pentachlorophenol by an Axenic Bacterial Culture," *Applied Microbiol.* 23:1033–1035 (May 1972).

Hou, C. T., et al., "Epoxidation of Short-Chain Alkenes by Resting-Cell Suspensions of Propane-Grown Bacteria," *Applied and Environ. Microbiol.* 46:171–177 (Jul. 1983).

Colby, J., Dalton, H. and Whittenbury, R., "An Improved Assay for Bacterial Methane Mono-Oxygenase: Some Properties of the Enzyme from Methylomonas methanica," *Biochem. J.* 151:459–462 (1975).

Colby, J. and Dalton, H., "Some Properties of a Soluble Methane Mono-Oxygenase from Methylococcus capsulatus Strain Bath," *Biochem. J.* 157:495–497 (1976).

Tonge, G. M., Harrison, D. E. F. and Higgins, I. J., "Purification and Properties of the Methane Mono-Oxygenase Enzyme System from Methylosinus trichosporium OB3b," *Biochem. J.* 161:333–344 (1977).

Patel, R. N. and Savas, J. C., "Purification and Properties of the Hydroxylase Component of Methane Monooxygenase," *J. Bacteriol.* 169:2313–2317 (May 1987).

Ghosal, D., et al., "Microbial Degradation of Halogenated Compounds," *Science* 228:135–142 (Apr. 1985).

Abelson, P. H., "Treatment of Hazardous Wastes," *Science* 233:509 (Aug. 1986).

Abelsom, P. H., Extract from a proposed manuscript, (Jan. 1987).

Barrio-Lage, G. A., Parsons, F. Z. and Lorenzo, P. A., "Inhibition and Stimulation of Trichloroethylene Biodegradation in Microaerophilic Microcosms," *Environ. Toxicol. and Chem.* 7:889–895 (1988).

(List continued on next page.)

OTHER PUBLICATIONS

Rintala, J. and Vuoriranta, P., "Anaerobic-Aerobic Treatment of Thermomechanical Pulping Effuents," *Tappi Journal* (Sep. 1988).

Wilson, J. T., et al., "Transport and Fate of Selected Organic Pollutants in a Sandy Soil," *J. Environ. Qual.* 10:501-506 (1981).

Woodward, R. E., "Destroying Toxic Waste by Bioremediation: The Process Works" (unknown origin and date).

Dean-Ross, D., "Biodegradation of Toxic Wastes in Soil," *ASM News* 53:490-492 (1987).

Tsien, H-C et al., "Biodegradation of Trichloroethylene by *Methylosinus trichosporium* OB3b," *Appl. Environ. Microbiol.* 55:3155-3161 (1989).

Oldenhuis, R. et al., "Degradation of Chlorinated Aliphatic Hydrocarbons by *Methylosinus trichosporium* OB3b Expressing Soluble Methane Monooxygenase," *Appl. Environ. Microbiol.* 55:2819-2826 (1989).

Strandberg, G. W. et al., "Degradation of Trichloroethylene and trans-1,2-Dichloroethylene by a Methanotrophic Consortium in a Fixed-Film, Packed-Bed Bioreactor," *Environ. Sci. Technol.* 23:1422-1425 (1989).

Uchiyama, H. et al., "Aerobic Degradation of Trichloroethylene at High Concentration by a Methane-Utilizing Mixed Culture," *Agric. Biol. Chem.* 53:1019-1024 (1989a).

Henson, H. et al., "Metabolism of Chlorinated Methanes, Ethanes, and Ethylenes by a Mixed Bacterial Culture Growing on Methane," *J. Ind. Microbiol.* 4:29-35 (1989).

Uchiyama, H. et al., "Aerobic Degradation of Trichloroethylene by a New Type II Methane-Utilizing Bacterium, Strain M," *Agric. Biol. Chem.* 53:2903-2907 (1989b).

Hanson, R. S. et al., "Development of Methanotrophs for the Biodegradation of Trichloroethylene and Other Chlorinated Olefins," *Abstr. Pap. Am. Chem. Soc.*, 1989 Meeting (1989).

Mayer, K. P. et al., "Degradation of Trichloroethylene by Methanotrophic Bacteria in a Laboratory Column of Saturated Aquifer Material," *Water Sci. Tech.* 20:175-178 (1988).

Thomas, J. M. and Ward, C. H., "In situ Biorestoration of Organic Contaminants in the Subsurface," *Environ. Sci. Technol.* 23:760-766 (1989).

Dooley-Danna, M. et al., "The Sequential Anaerobic-/Aerobic Biodegradation of Chlorinated Ethenes in an Aquifer Simulator," *Abstr. Annu. Meet. Am. Soc. Microbiol.*, 1989 Meeting (1989).

Eng, W. and Palumbo, A. V., "Trichloroethylene and Trans-1,2-dichloroethylene Degradation by Pure Methanotrophic Cultures and Mixed Methane-Utilizing Consortia," *Abstr. Annu. Meet. Am. Soc. Microbiol.*, 1989 Meeting (1989).

Henry, S. M. et al., "Effects of Mineral Medium on Trichloroethylene Oxidation and Involvement of a Particulate Methane Monooxygenase," *Abstr. Annu. Meet. Am. Soc. Microbiol.*, 1989 Meeting (1989).

Moore, A. T. et al., "Biodegradation of trans-1,2-Dichloroethylene by Methane-Utilizing Bacteria in an Aquifer Simulator," *Environ. Sci. Technol.* 23:403-406 (1989).

Janssen, D. B. et al., "Degradation of trans-1,2-Dichloroethene by Mixed and Pure Cultures of Methanotrophic Bacteria," *Appl. Microbiol. Biotechnol.* 29:392-399 (1988).

Nelson, M. J. K. et al., "Preliminary Development of a Bench-Scale Treatment System for Aerobic Degradation of Trichloroethylene," *Basic Life Sci.* 45:203-209 (1988).

Meyer, P. and Bartha, R., "Effects of Analog Substrates, Methanogens and Methanotrophs on the Persistence of 2,3,7,8-Tetrachlorodibenzo-p-dioxin (TCDD),a" *Abstr. Annu. Meet. Am. Soc. Microbiol.*, 1988 Meeting (1988).

Roberts, P. V. et al., *In-situ Aquifer Restoration of Chlorinated Aliphatics by Methanotrophic Bacteria*, Report No. EPA/600/2-89/033 (1989).

Donaldson, T. L. et al., *Biotreatment of TCE (Trichloroethylene) Contaminated Groundwater*, Report No. CONF-890430-3 (1989).

Semprinni, L. et al., "In Situ Biodegradation for Aquifer Restoration," *Environ. Waste Mgt. Mag.* (Apr. 1990), pp. 22-23.

Leisinger, T., "Microbial Degradation of Chlorinated Alkanes and Alkenes," *Eur. Conf. Biotechnol.* (1988), pp. 150-154.

Strandberg, G. W. et al., *Degradation of Trichloroethylene and Trans-1,2-Dichloroethylene by a Methanotrophic Consortia in a Trickle-Type Bioreactor*, Report No. CONF-881054-23 (1988).

(List continued on next page.)

OTHER PUBLICATIONS

Barrio-Lage et al., "Sequential Dehalogenation of Chlorinated Ethenes," *Environ. Sci. Technol.* 20:96-99 (1986).

Barrio-Lage et al., "Kinetics of the Depletion of Trichloroethene," *Environ. Sci. Technol.* 21:366-370 (1987).

Kloepfer et al., "Anaerobic Degradation of Trichloroethylene in Soil," *Environ. Sci. Technol.* 19:277-280 (1985).

Khare and Dondero, "Fractionation and Concentration from Water of Volatiles and Organics on High Vacuum System: Examination of Sanitary Landfill Leachate," *Environ. Sci. Technol.* 11:814-819 (1977).

Parsons et al., "Transformations of Tetrachloroethene and Trichloroethene in Microcosms and Groundwater," *Jour. A.W.A.A.*, Feb., 1984:56-59.

Parsons and Lage, "Chlorinated Organics in Simulated Groundwater Environments," *Jour. A.W.W.A.*, May, 1985:52-59.

Petura, "Trichloroethylene and Methyl Chloroform in Groundwater: A Problem Assessment," *Jour. A.W.-W.A.*, Apr., 1981:200-205.

Tabak et al., "Biodegradability Studies With Organic Priority Pollutant Compounds," *Jour. W.P.C.F.* 53:1503-1518 (1981).

Wilson et al., "Biotransformations of Selected Alkylbenzenes and Halogenated Aliphatic Hydrocarbons in Methanogenic Aquifer Material: A Microcosm Study," *Environ. Sci. Technol.*, 20:997-1002 (1986).

Trussell et al., "Precise Analysis of Trihalomethanes," *Jour. A.W.W.A.*, Jul., 1979:385-396.

Brunner et al., "Bacterial Degradation of Dichloromethane," *Appl. Environ. Microbiol.* 40:950-958 (1980).

Brown et al., "Pentachlorophenol Degradation: A Pure Bacterial Culture and an Epilithic Microbial Consortium," *Appl. Environ. Microbiol.* 52:92-97 (1986).

Boyd et al., "Anaerobic Biodegradation of Phenolic Compounds in Digested Sludge," *Appl. Environ. Microbiol.* 46:50-54 (1983).

Deeley et al., "Biodegradation of [14C] Phenol in Secondary Sewage and Landfill Leachate Measured by Double-Vial Radiorespirometry," *Appl. Environ. Microbiol.* 49:867-869 (1985).

Petrasek et al., "Fate of Toxic Organic Compounds in Wastewater Treatment Plants," *Jour. W.P.C.F.* 55:1286-1296 (1983).

Young and Rivera, "Methanogenic Degradation of Four Phenolic Compounds," *Water Res.* 19:1325-1332 (1985).

Grbic-Galic and Vogel, "Transformation of Toluene and Benzene by Mixed Methanogenic Cultures," *Appl. Environ. Microbiol.* 53:254-260 (1987).

Healy and Young, "Anaerobic Biodegradation of Eleven Aromatic Compounds to Methane," *Appl. Environ. Microbiol.* 38:84-89 (1979).

Boethling and Alexander, "Effect of Concentration of Organic Chemicals on Their Biodegradation by Natural Microbial Communities, *Appl. Environ. Microbiol.* 37:1211-1216 (1979).

Suflita et al., "Kinetics of Microbial Dehalogenation of Haloaromatic Substrates in Methanogenic Environments, *Appl. Environ. Microbiol.* 45:1466-1473 (1983).

Brown, "Household Hazardous Waste: The Unresolved Water Quality Dilemma," *Jour. W.P.C.F.* 59:120-124 (1987).

DeWalle and Chian, "Detection of Trace Organics in Well Water Near a Solid Waste Landfill," *Jour. A.W.-W.A.*, Apr., 1981:206-211.

Vogel and Grbic-Galic, "Incorporation of Oxygen From Water Into Toluene and Benzene During Anaerobic Fermentative Transformation," *Appl. Environ. Microbiol.* 52:200-202 (1986).

Geraghty and Miller, "Status of Groundwater Contamination in the U.S.," *Jour. A.W.W.A.*, Mar., 1978:162-167.

Harmsen, "Identificatioon of Organic Compounds in Leachate From A Waste Tip," *Water Res.* 17:699-705 (1983).

Keith and Telliard, "Priority Pollutants I-A Perspective View," *Environ. Sci. Technol.* 13:416-423 (1979).

Kim and Maier, "Acclimation and Biodegradation of Chlorinated Organic Compounds in the Presence of Alternate Substrates," *Jour. W.P.C.F.* 58:157-164 (1986).

Kobayashi and Rittman, "Microbial Removal of Hazardous Organic Compounds," *Environ. Sci. Technol.* 16:170A-183A (1982).

Morgan, "Floating Chains and Fine Bubbles Improve Lagoon Aeration Methods," *Pulp & Paper*, Apr., 1987:87-88.

Tittlebaum, "Organic Carbon Content Stabilization Through Landfill Leachate Recirculation," *Jour. W.P.C.F.* 54:428-433 (1982).

AEROBIC BIOLOGICAL DEHALOGENATION REACTOR

FIELD OF THE INVENTION

This invention relates to the aerobic biodegradation of organic compounds in an aqueous mixture. In particular, the aqueous mixture is passed through an aerobic bioreactor containing a mixed microbial population, including methylotrophic microorganisms, supported on a solid substrate bed. The population of microorganisms dehalogenates and biodegrades the organic compounds in the mixture by way of co-metabolic and other metabolic processes.

BACKGROUND OF THE INVENTION

As world population and industrial development have increased in the face of progressively stricter regulation and enforcement of environmental standards, substantial work has been directed toward effective processes for purifying soil and water polluted by organic chemicals. Some of these processes are aimed at cleaning up soils and water contaminated by prior discharges of waste organic compounds from industry and agriculture. Other processes are aimed at minimizing further release of such compounds into the environment. Many such processes are ineffective because a number of organic compounds, especially various halogenated species, are refractory, being resistant to biological or chemical attack by existing means or unless excessive amounts of energy are expended. Unfortunately, many halogenated organic compounds are toxic; some are known or suspect carcinogens or mutagens. Hence, as these compounds become more widespread in soil and water around the world, the need for efficacious and inexpensive methods for treating such wastes becomes increasingly urgent.

Halogenated organic compounds can be separated from aqueous liquids by conventional technology. However, the process is expensive and still results in a complex mixture of halogenated compounds that must be purified from one another to be of any practical use. Unless the constituent compounds can be repurified for further industrial use, such mixtures of halogenated organic compounds remain a waste material that presents a serious disposal problem.

Some existing processes have employed various types of microorganisms to degrade the pollutants biologically. For example, U.S. Pat. No. 4,401,569 to Jhaveri et al. discloses a method and apparatus for treating ground water contaminated with certain halogenated hydrocarbons. In the Jhaveri process, ground water is removed and stored in a holding tank from which the water is delivered to a biostimulation tank. The biostimulation tank contains microorganisms naturally occurring at the contamination site or introduced thereto, which utilize the particular organic pollutant(s) as a source of carbon and energy. Nutrients, including certain inorganic salts and other unspecified nutrients, are added to the biostimulation tank to accelerate the organisms' metabolism of the pollutants. The biostimulation tank is also aerated with oxygen and/or other unspecified gas. Over time, biodegradation processes decrease the concentrations of organic pollutants in the water in the biostimulation tank. After a length of time, the treated water is transferred to a settling tank where further nutrients are then added to the treated water and from which the water is returned to the soil at the contamination site. Oxygen and/or other unspecified gases are also injected into the soil at the return site. Thus, the Jhaveri et al. patent is primarily concerned with a batch process for the biological removal of certain hydrocarbons from contaminated soil and ground water. Jhaveri et al. do not disclose or suggest supporting methylotrophic microorganisms on a solid substrate bed through which an aqueous mixture containing organic compounds is passed for biodegrading the compounds.

U.S. Pat. No. 4,713,343 of Wilson, Jr. et al. relates to a process for aerobic biodegradation of certain low-molecular-weight halogenated aliphatic hydrocarbons in water using methanotrophic bacteria. The Wilson, Jr. et al. patent is purportedly applicable to the treatment of contaminated drinking water, ground water and industrial wastewater. In the Wilson, Jr. et al. process, methanotrophic bacteria present in soil and water are exposed to oxygen or air and a low concentration of a low-molecular-weight alkane, such as methane or natural gas. Wilson, Jr. et al. mention that the process can occur in any material that can be colonized by alkane-oxidizing bacteria. In one approach, natural gas and air are dissolved in water containing the bacteria and a specific halogenated aliphatic hydrocarbon. After a time, the bacteria degrade the hydrocarbon in the water. Wilson, Jr. et al. specifically disclose a batch process of removing ground water from a site having contaminated soil, treating the water in the above manner, and returning the water to the ground. They also disclose an in situ approach wherein water containing dissolved air and the low-molecular-weight alkane is injected deep into contaminated soil to stimulate indigenous bacteria to degrade the soil contaminant.

Wilson, Jr. et al. describe quantitative results obtained only with laboratory-scale mockups of the in situ approach wherein soil was packed in a glass column to a depth of 150 cm. A stream of air containing 0.6 percent natural gas by volume was passed over the head of the column. Following a three-week acclimation, water containing trichloroethylene was applied to the column at the rate of 21 cm$^3$ per day. Most of the trichloroethylene in the water was biodegraded.

U.S. Pat. No. 4,385,121 of Knowlton also discloses the use of soil microorganisms to biodegrade hydrocarbon contaminants in the soil. The Knowlton patent describes a land-farming process in which at least one of a spent, solid, particulate porous, hydrocarbon cracking catalyst or a spent, solid, porous particulate filtration medium is tilled or otherwise incorporated into soil contaminated with hydrocarbon wastes. The microorganisms in the soil then biodegrade the waste hydrocarbons. The addition of catalyst or filtration medium improves aeration necessary for supporting microorganism metabolism.

Hence, although prior art approaches are known, a need exists for an improved method and apparatus for biodegrading organic compounds in aqueous mixtures, especially for dehalogenating and further biodegrading recalcitrant halogenated organic wastes, including chlorinated organic compounds, as they are generated by industrial plants.

SUMMARY OF THE INVENTION

In accordance with the present invention, a biological reactor for dehalogenating and biodegrading waste organic compounds present in a water mixture (liquid phase) has a mixed microbial population including methylotrophic microorganisms supported on a solid substrate bed in a reactor housing. The substrate bed is preferably made of a manufactured solid material, such as activated carbon particles, having a larger specific surface area and less resistance to hydraulic flow therethrough than natural materials such as soil. In one preferred form of this invention, a low-molecular-weight alkane is flowed through the liquid phase either prior to or in the bed to provide a carbon and energy source for the methylotrophic microorganisms. The flow rate of the low-molecular weight alkane is preferably sufficient to maintain at least a minimum concentration of the alkane throughout the substrate bed. In reactors containing a significant population of methanotrophic microorganisms (a sub-class of methylotrophic microorganisms), the low-molecular-weight alkane is substantially methane. In addition to the low-molecular-weight alkane, a second gas consisting at least partially of oxygen is also flowed through the liquid phase either prior to or in the bed. The flow rate and oxygen concentration of the second gas is preferably sufficient to achieve at least a minimal concentration of dissolved oxygen to maintain aerobic conditions substantially throughout the bed. The aqueous liquid mixture containing halogenated and other organic compounds is passed through the bed wherein the microorganisms aerobically metabolize the organic compounds in the mixture along with the low-molecular-weight alkane. Such metabolism includes co-metabolic processes that dehalogenate, including dechlorinate, the organic compounds in the liquid mixture.

As another aspect of the invention, the solid substrate bed may be formed of activated carbon granules which are preloaded with organic compounds, or which are entirely "spent" with regard to adsorptive capacity. In such a case, the adsorbed compounds in the bed serve as a carbon and energy source for certain of the microorganisms, thereby particularly enhancing rapid colonization of the bed with the microorganisms when the bioreactor is initially placed in use. The adsorbed compounds also appear to enhance the stable operation of the bioreactor during variable influent conditions.

As another feature of the present invention, the aqueous mixture may optionally be treated to remove solids, indigenous biomass, and excess biochemical oxygen demand (BOD) from the mixture prior to delivering the mixture to the bed. BOD reduction reduces the concentrations of carbonaceous nutrients and minimizes the risk of clogging of the bed with excessive biological growth, which excessive growth can cause the development of undesirable anaerobic conditions in the bed.

As a further feature of the present invention, optional bed-cleaning mechanisms may be employed to remove excess biomass from the bed if clogging is evident. In one approach, a mechanism is provided for fluidizing the bed to facilitate flushing of the bed with liquid. In another approach, portions of the bed are selectively removed, cleaned, and returned to the bed. Preferably, the removed portions of the bed are taken from an upstream portion of the bed where biomass-laden solids are more likely to accumulate.

Although the present invention can be used in a batch mode, as another feature of the present invention, the bioreactor may be coupled to the effluent line of an industrial plant for continuously receiving and treating wastewater containing organic compounds from the plant. It has been found that effective wastewater treatment occurs even though the concentration of organic compounds in the industrial plant effluent varies during normal operation of the plant.

As yet another aspect of the present invention, the microbial population dispersed throughout the substrate bed is heterogeneous. The population includes plural species of methylotrophic microorganisms as well as other types of microorganisms. An inoculum of such a heterogeneous microbial population can be obtained from a native population of such organisms occupying a depth zone between an underlying anaerobic benthal layer and an overlying aerobic layer of a pond having such layers. The term "pond" encompasses marshes, swamps, wastewater treatment lagoons, and any other bodies of water having an organic-rich anaerobic benthal layer and an aerobic aqueous layer. After the inoculum is introduced into the substrate bed, the microorganisms in the inoculum quickly colonize and proliferate throughout the bed. The microorganisms become quickly acclimated by recirculating a volume of the aqueous mixture which is to be treated through the bed as the colonization takes place. Such colonization and acclimation is rapid, even when the aqueous mixture is a heavily polluted industrial waste.

A wide variety of organic compounds, including alkanes, alkenes, aromatic hydrocarbons and halogenated derivatives of such compounds, either alone or in complex mixtures, are biodegraded in the biological reactor of the present invention. The term "biodegradation" includes metabolic decomposition of the organic compounds into smaller and/or simpler molecules. Biodegradation also includes dehalogenation: the removal of halogen atoms, such as chlorine atoms, from halogenated organic compounds. For example, in one series of tests, substantial decreases in the concentration of pentachlorophenol in an effluent mixture from an industrial plant were achieved with the bioreactor of the present invention. Dechlorination of the pentachlorophenol (PCP) was evidenced by a substantial decrease in the concentration of total soluble adsorbable organic chloride with a concomitant increase in the concentration of inorganic chloride as the mixture flowed through the bioreactor. Biodegradation of the aromatic moiety was evidenced by direct measurements of PCP concentrations in influent and effluent liquid flowing through the reactor. Biodegradation of PCP was also evidenced by a substantial decrease in ultraviolet absorption at 254 nanometers of the pentachlorophenol-containing mixture after passing through the bed, indicating fission of the benzene ring. Limited testing has also shown that the biological reactor of the present invention can be used to biodegrade dioxin in the aqueous mixture.

As another feature of the invention, a secondary biological reactor containing anaerobic methanogenic microorganisms may be used to produce at least a portion of the methane gas required by a primary aerobic biological reactor according to the present invention containing methanotrophic microorganisms. Also, a portion of the dehalogenated liquid effluent from the primary aerobic biological reactor may be diverted to the secondary reactor as a source of carbon and energy for the methanogenic microorganisms in the secondary anaerobic reactor.

It is accordingly one object of the present invention to provide an improved method and apparatus for dehalogenating and further biodegrading a wide variety of organic compounds present in an aqueous mixture, including such compounds as pentachlorophenol and dioxin.

Another object of the present invention is to provide a method and apparatus employing a mixed microbial population including methylotrophic organisms for aerobically dehalogenating and further biodegrading organic compounds at a relatively high rate.

Still another object of the present invention is to provide a method and apparatus which use a solid substrate material having a high specific surface area and containing adsorbed organic compounds as a supporting bed for a mixed microbial population that includes methylotrophic microorganisms.

A further object of the present invention is to provide a biological reactor which is sufficiently small to be portable, and yet which is capable of treating relatively large volumes of aqueous mixtures contaminated with organic compounds, including halogenated organic compounds, in either a batch or continuous process.

Another object of the present invention is to provide a method and apparatus for continuously treating a complex, organic-laden effluent from an industrial plant, including such effluents having variable concentrations of waste organic compounds.

Still another object of the present invention is to provide a biological reactor which is cost-effective to manufacture, maintain and use.

A still further object of the present invention is to provide a biological reactor which is safe to use.

These and other objects, features and advantages of the present invention will become apparent with reference to the following description and drawings.

DETAILED DESCRIPTION OF PREFERRED EMBODIMENTS

The present invention is concerned with a method and apparatus for the aerobic dehalogenation and further biodegradation of certain organic compounds found in an aqueous mixture to effectively remove these contaminating compounds from the mixture. Aqueous mixtures with which the invention is concerned may include natural surfaces waters, drinking water, ground water, leachates from landfills, industrial wastewaters, and waters such as those produced by an interdiction well designed to intercept and remove a plume of contaminated ground water. The present invention is particularly applicable to the treatment of industrial wastewaters containing chlorinated organic compounds as the wastewaters are generated by an industrial facility. Broadly, however, the invention is concerned with the treatment of water to remove the indicated contaminants, regardless of the source or location of the water, and regardless of whether the treatment is a batch or continuous process.

Figure 1:
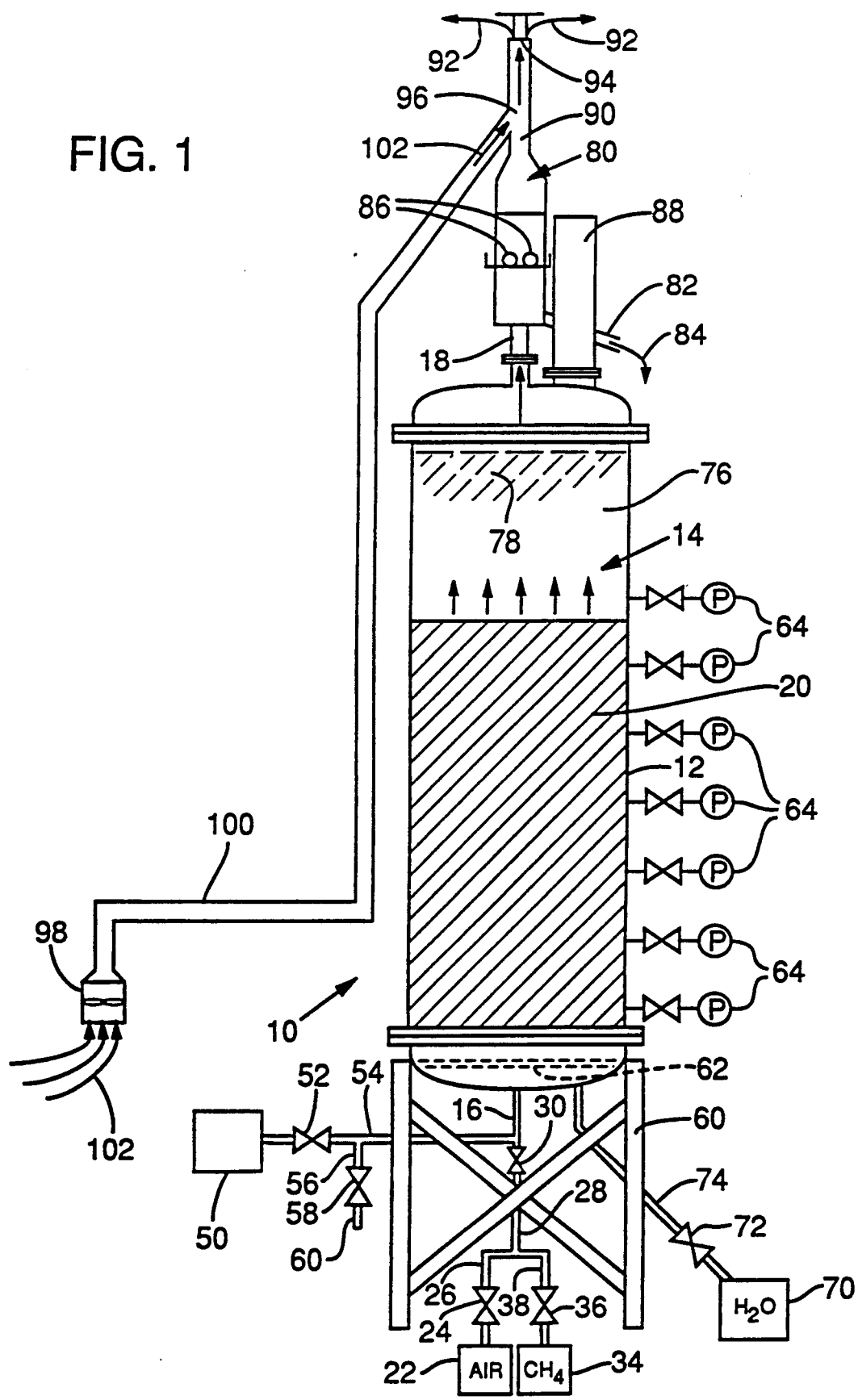
FIG. 1 is a schematic front elevational view of one form of biological reactor in accordance with the present invention.

With reference to FIG. 1, one form of biological reactor 10 in accordance with the present invention includes a hollow cylindrical upright housing 12, which defines an interior chamber 14. Housing 12 has a lower inlet 16 and an upper outlet 18, with chamber 14 positioned between lower inlet 16 and upper outlet 18. The housing 12 may be of a corrosion-resistant material, such as stainless steel.

A substrate bed 20 for supporting a mixed microbial population that includes methylotrophic microorganisms is positioned within chamber 14. The substrate bed 20 may be of any solid or rigid material which will support films and colonies of the microorganisms growing thereon. Preferably, the substrate bed 20 is made from certain manufactured materials having a large specific surface area and a low resistance to hydraulic flow therethrough. Manufactured materials broadly encompass materials other than naturally occurring materials such as soil in its natural state. Crushed, sized, or otherwise processed materials are examples. As other examples, the substrate bed may be comprised of particles of glassy, ceramic or calcined inorganic materials, or of polymeric plastic materials such as polyethylene or polypropylene. One suitable material for the substrate bed is granular activated carbon, the grains having a size which, for example, range from 8×30 mesh to 12×40 mesh.

For optimal colonization and acclimation by the microorganisms of a substrate bed having adsorptive capacity, such as activated carbon, the bed material may be preloaded with organic compounds. In the case of granular activated carbon, such preloaded material may include "spent" granules, which means that the adsorbing capacity of the granules is at or near saturation. Since spent activated carbon is usually disposed of after it becomes nonregenerable and has little or no value (or even requires a significant disposal cost), the bioreactor of the present invention thus provides an economically practical use for this material. The granular activated carbon may also be pre-adsorbed by contacting it for a period of time with the particular wastewater to be treated by the bioreactor of the present invention. Organic compounds pre-adsorbed onto bed material having adsorptive capacity also provide an additional carbon source for the microorganisms living thereon, which facilitates rapid colonization of the bed 20. Organic compounds not dissolved in water are not readily available for biodegradation, but it appears that a substantial portion of the organic compounds adsorbed on the bed material are available.

Adsorption and desorption of organic compounds on a bed material having adsorptive capacity for organic compounds is also a concentration-dependent equilibrium phenomenon. The bed material adsorbs organic compounds during conditions when the concentration of such compounds in the liquid passing through the bed is high. The bed material releases, or desorbs, some of the organic compounds when the concentration in the liquid passing into the bed is lowered. In such a manner, a bed having adsorptive capacity for organic compounds also serves to buffer the stable performance of the biological reactor against the effect of widely varying flow rate and concentration of the aqueous mixture flowing through the substrate bed.

The mixed population of microorganisms colonized throughout the bed 20 dehalogenate and biodegrade certain organic compounds from an aqueous mixture passing therethrough contaminated with organic compounds. Liquid is maintained in the bed 20 to provide a suitable aqueous environment for the microorganisms. The mixed microbial population includes methylotrophic microorganisms. In one preferred form of the invention, the microorganisms include methanotrophic microorganisms, the latter being a subclass of methylotrophs. The biological reactor of the present invention functions optimally under conditions favoring a microbial population throughout the bed enriched with methanotrophs. However, a microbial population predominantly methylotrophic will also serve well. In either case, both methylotrophic and methanotrophic species seem to be present in bed inocula (see below) and will proliferate throughout the bed.

Methylotrophs as a general group are physiologically distinctive, capable of utilizing methane and other lower molecular weight alkanes, in particular, those containing one to four carbon atoms, as sole sources of carbon and energy. These organisms are widely distributed in aquatic environments and are taxonomically diverse, including certain bacteria and possibly other types of microorganisms. All known methylotrophic bacteria are gram negative, facultative aerobes and exist in a variety of shapes.

Methanotrophic microorganisms are obligate in their use of methane, being able to use as a carbon and energy source only compounds containing no C—C bonds. They are indigenous to soil and to aquatic environments having sufficient methane and oxygen concentrations for their growth. Natural aquatic environments where such microorganisms are found include swamps, cattail marshes, lakes and ponds. In these environments, methane is produced from anaerobic decomposition of dead plant and animal matter and various other organic compounds, particularly by methanogenic microorganisms. The methanotrophic microorganisms are usually present as a heterogeneous population in a given environment, where the species profile, which includes methanotrophs, other methylotrophs, and various heterotrophic microorganisms, is determined by the prevailing types and levels of organic compounds, other nutrients, and gases. Such a mixed culture tends to be somewhat symbiotic, where each type of microorganism utilizes one or more metabolic by-products of another type of microorganism.

Methanotrophic microorganisms also oxidize other organic compounds via a process termed "co-metabolism." Co-metabolism is the transformation of a non-growth compound in the obligate presence of a growth compound or another transformable compound. Dalton and Stirling, *Phil. Trans. R. Soc. Lond.* 8297:481 (1982). Co-metabolism by methanotrophs is catalyzed by the methane-monooxygenase (MMO) enzyme system. MMO catabolism of methane proceeds via a four-step enzymatic pathway by which methane is oxidized in the obligate presence of oxygen to carbon dioxide, with methanol being a principal intermediate. MMO is nonspecific as to enzyme substrate, gratuitously oxidizing, in the presence of methane and oxygen, a wide variety of other organic compounds, including alkanes, alkenes, ethers and aromatics, even though the methanotrophic microorganisms cannot utilize many of the metabolic products. MMO also oxidizes chlorinated organic compounds, rendering them more susceptible to biodegradation by heterotrophic microorganisms. One possible mechanism for MMO oxidation of chlorinated organics is the conversion to an epoxide, liberating inorganic chloride. The epoxide is then rearranged or hydrolyzed to produce compounds for heterotrophs.

Generally, an increase over a defined range in the concentration of methane and oxygen in a microbial environment leads to an increase in methane metabolism by methanotrophs and a fortuitous increase in the oxidation of other organic compounds. During conditions of elevated methane concentrations, as the methanotrophic microorganisms produce increased amounts of various oxidized compounds from MMO co-metabolism, the population of other methylotrophic and various heterotrophic microorganisms also increases, deriving carbon and energy from compounds partially oxidized by the methanotrophs. Such cooperative dehalogenation and biodegradation by a mixed microbial population is termed "biotransformation."

Methylotrophic microorganisms other than methanotrophs are less obligate than methanotrophs. Methylotrophs can utilize various lower molecular weight alkanes, particularly saturated $C_1$ and $C_4$ compounds, as well as MMO intermediates such as methanol, as sources of carbon and energy. Methylotrophs, like methanotrophs, also co-metabolize other organic compounds via enzymatic processes involving MMO and probably other enzyme systems. As with methanotrophs, an increase over a defined range in the concentrations of oxygen and $C_1$–$C_4$ alkanes and/or methanol leads to an increase in the fortuitous oxidation of other organic compounds, including halogenated organic compounds.

One environment where various methylotrophic (including methanotrophic) microorganisms have been found in large numbers is in the intermediate layer between an underlying benthal layer and the overlying aerobic layer in a marsh or pond having such layers. Such layers, including the methylotroph-rich intermediate layer, are also found in bioponds used for treatment of effluent from industrial plants, such as pulp and paper mills, including bleach mills utilizing chlorine and chlorine compounds.

A heterogeneous population of methanotrophic microorganisms, including methylotrophs, methanotrophs, and associated heterotrophs obtained as an inoculum from a native environment are capable of adhering to and proliferating on a supportive substrate if oxygen and the appropriate source of carbon and energy are provided. Thus, these microorganisms are capable of colonizing the bed 20. Inocula of such a mixed microbial population can be obtained either from a natural source such as a pond or marsh, or from an aerobic waste treatment lagoon or "biopond." Each inoculum will have a particular distribution of microbial species, depending upon the concentration of oxygen and upon the types and concentrations of other organic compounds, inorganic nutrients, as well as temperature and the pH of the source. In fact, an inoculum having a species profile "tailored" for a particular mixture of organic compounds to be biodegraded can be obtained by procuring the inoculum from an aerobic biopond exposed to the same or similar waste material as that to be biodegraded by the microorganisms on the substrate bed. By increasing the concentrations of oxygen and whatever low-molecular-weight alkane is used as a carbon and energy source flowing through a substrate bed colonized by the inoculum, it is possible to significantly enhance the rate at which the microorganisms biodegrade the organic compounds.

In the illustrated FIG. 1 embodiment, the gas containing oxygen is derived from a source of air or oxygen 22 which is coupled through a valve 24, a first conduit section 26, a second conduit section 28, another valve 30, and to the inlet 16 of the housing 12. Although oxygen gas is preferred, air will result in satisfactory performance of the bioreactor. Typically, valve 24 comprises a flow control valve and is used to establish the rate at which air or oxygen is delivered to the housing 12. For optimum operation, the concentration and flow rate of the oxygen-containing gas through the bed should be sufficient to maintain aerobic conditions throughout the bed. One method of achieving the desired oxygen concentration throughout the bed, especially with longitudinally extended substrate beds, is to inject the oxygen-containing gas into the aqueous liquid mixture while the liquid mixture is pressurized above atmospheric pressure, before the liquid enters housing 12 (details not shown). Such high-pressure injection supersaturates the concentration of oxygen in the aqueous liquid mixture, causing some outgassing of oxygen as the liquid subsequently flows at atmospheric pressure through the bed. Such outgassing allows the liquid to convey and deposit microbubbles of oxygen to substantially all portions of the bed where the bubbles become available for redissolution into the liquid as necessary, ensuring an adequate supply of oxygen for the microorganisms throughout the bed. It is also well known that molecular oxygen is absorbed onto activated carbon and thus affords as additional oxygen reservoir. Also, the oxygen can be simply flowed through the bed or otherwise injected into the bed. To the extent microbubbles of oxygen are formed, the microbubbles assist in supplying oxygen substantially through the entire bed.

A source of methane or other low-molecular-weight alkane 34 is coupled through a flow control valve 36, a conduit section 38, the conduit section 28 and through valve 30 to the housing inlet 16. To enhance methanotrophic microorganism populations in the bed, the source 34 of the alkane gas may comprise a source of methane gas, such as natural gas from a natural gas line. Commercially available American natural gas usually consists of approximately 85% methane, 9% ethane, 3% propane and 1% butane. A biological methanogenic reactor is still another example of a source of methane and is described below in connection with FIG. 6.

The flow rate of the low-molecular-weight alkane through the bed should be sufficient to maintain an adequate carbon and energy source for the methylotrophic microorganisms throughout the bed. One method of increasing the concentration of the alkane throughout the bed, especially with longitudinally extended substrate beds, is to inject the alkane as a gas into the aqueous liquid mixture while the liquid is pressurized above atmospheric pressure, before the liquid enters housing 12 (details not shown). Such high-pressure injection supersaturates the concentration of the alkane, causing some outgassing thereof as the liquid subsequently flows at atmospheric pressure through the bed. Such outgassing allows the liquid to convey and deposit microbubbles of the alkane to all portions of the bed where the bubbles become available for redissolution into the liquid as necessary, ensuring an adequate carbon and energy source for the microorganisms throughout the bed. Testing with methane has shown that the available concentration of the low-molecular-weight alkane throughout the bed should be at least 0.1 mg/L to retain viability of the microorganisms. Higher concentrations are required for optimal performance pressure-injecting the gaseous alkane as described above can raise the concentration to 200 mg/L or higher Also, the alkane may simply be flowed through or injected into the bed under atmospheric pressure Microbubbles of alkane that happen to form aid in supplying the alkane substantially throughout the entire bed.

Referring further to FIG. 1, the aqueous mixture containing the organic compounds which are to be treated by the biological reactor 10 are delivered from a source 50 through a flow control valve 52 and a conduit section 54 to the housing inlet 16. Source 50 may be any source of contaminated aqueous liquid such as drinking water, ground water, industrial wastewater, leachates from landfills, contaminated liquids in drums, and so forth. For purposes of discussion, and without limiting the scope of the invention, the following description assumes that source 50 is a wastewater effluent line of an industrial plant, such as a wood treatment plant, such plant producing chlorinated hydrocarbon wastes.

The housing 12 and bed 20 may be sized to treat the entire effluent from a wastewater line of the plant. Alternatively, line 54 may be coupled through a conduit 56, a flow control valve 58, and through a conduit 60 to additional bioreactors of the type illustrated in FIG. 1. By operating biological reactors in parallel, the size of the individual reactors may be reduced and the treatment capacity increased.

As a specific example, one biological reactor of the type shown in FIG. 1 was four feet in diameter and nine feet high, although a higher ratio of length to diameter would be more desirable. This reactor was filled with activated carbon and inoculated with microorganisms as follows. Using a benthal core sampler, samples of interfacial solids were removed from the top two inches of the benthal layer in an aerated waste treatment lagoon. The samples were taken from an area of the lagoon where most of the biochemical oxygen demand is removed from the liquid. Approximately three gallons of the benthal material was collected and kept on ice until used to seed the reactor bed. Forty-eight hours prior to filling the reactor housing 12 with saturated activated carbon, the chilled benthal solids were placed in a 55-gallon drum along with a volume of influent wastewater and approximately 20 gallons of saturated activated carbon. Air and natural gas were then bubbled through this mixture. The reactor housing 12 was loaded with approximately 800 gallons (approximately 10,000 pounds) of saturated activated carbon from a porthole (not shown) in the top of the reactor housing 12. As the saturated carbon was being added to the reactor, the seeded activated carbon from the drum was also added to the reactor housing 12 in successive alternating layers of seeded and unseeded activated carbon until the reactor housing 12 was filled. A volume of wastewater of the type to be ultimately treated by the bioreactor was recycled through the loaded bioreactor for five days, with simultaneous passage of methane and oxygen through the bed, to allow the inoculum of microorganisms to acclimate and proliferate throughout the substrate bed 20. Because wastewater from the source 50 is recycled vertically through the bed during the acclimation period, the acclimation process rapidly selects for a microbial species profile on bed 20 which is best able to thrive in the wastewater being treated.

After acclimation, the bioreactor of FIG. 1 was operated in a single-pass mode, receiving the intended effluent stream of wastewater. This specific reactor substantially reduced the concentration of chlorinated organic compounds in the wastewater, as described below in connection with, for example, FIGS. 7 and 8.

When describing the performance of biological reactors such as the FIG. 1 example, "detention time" rather than "flow rate" through the reactor is the preferred unit of comparison. Use of detention time better reflects the role of biochemical kinetics in the enzymatic breakdown of organic compounds flowing through the substrate bed. The typical flow rate through the reactor of FIG. 1 during various testing was one to three gallons per minute, although somewhat higher rates are possible. With an effective volume of liquid in the substrate bed of at least 300 gallons, the minimum detention time of liquid flowing through the bed at the three gallons per minute rate is at least 100 minutes, as confirmed in a residence time distribution study with a lithium tracer. Although detention times can be varied, it was found with such a flow rate and detention time that the majority of biodegradation occurred in the first two longitudinal feet of the reactor. These results indicate that similar flow rates can be treated with a biological reactor having only one-fourth the volume of the specific example tested.

The relatively small size of the reactor described herein renders it portable. It may be transported to any of various sites for use in treating contaminated wastewater. Typically, a stand 60 is used to support the reactor in a vertical position at the desired location.

Figure 2:
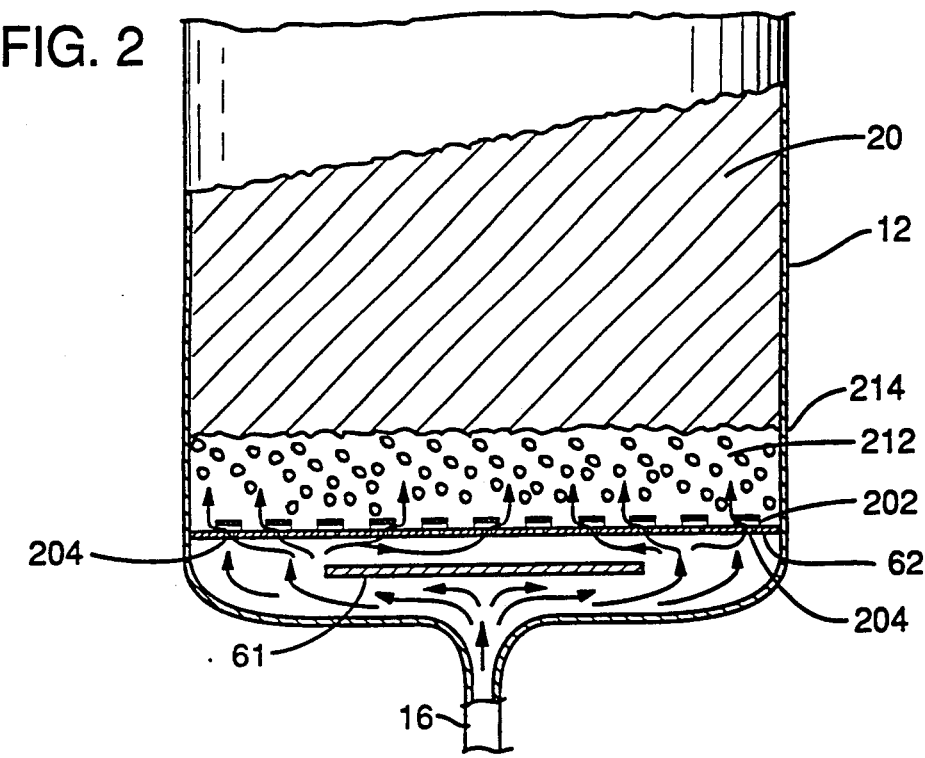
FIG. 2 is a front elevational view of the reactor of FIG. 1, with a portion of the housing 12 cut away, showing optional transverse baffle plates and directions of hydraulic flow therearound.
Figure 3:
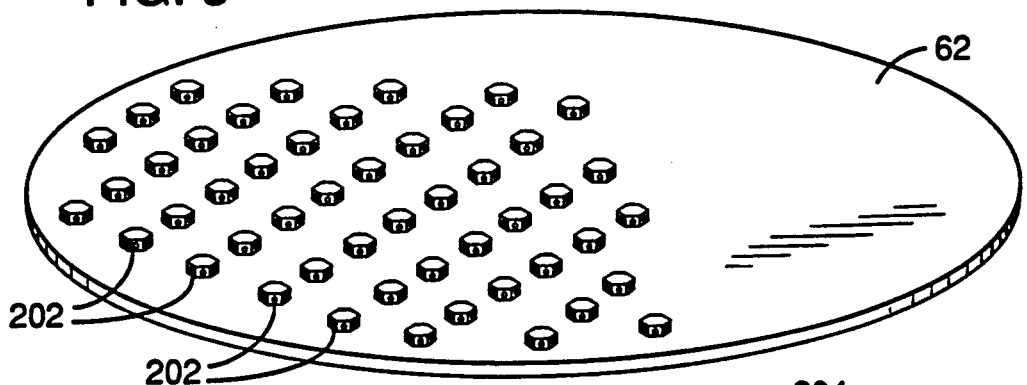
FIG. 3 is a detailed view of the transverse baffle plate of the FIG. 1 reactor.

As also shown in FIGS. 1 and 2, a mechanism is provided for dispersing the oxygen-containing gas, the low-molecular-weight alkane, and liquid flow substantially across the full diameter of the bed 20. This mechanism may take various forms including flow-directing baffles within chamber 14. As a specific example, the illustrated FIG. 2 mechanism comprises a pair of transverse plates 61 and 62, plate 62 having a uniform pattern of small perforations throughout the surface area of the plate. The distribution of gases and liquid flow across the bed diameter effectively minimizes the existence of "dead" zones or anaerobic zones in the bed, thereby maximizing the efficiency of the bioreactor.

Figure 4A:
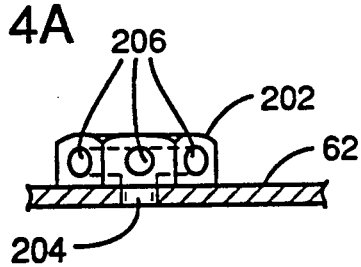
FIG. 4A is a side elevational view of a hexagonal member 202 mounted to the baffle plate of FIG. 3.
Figure 4B:
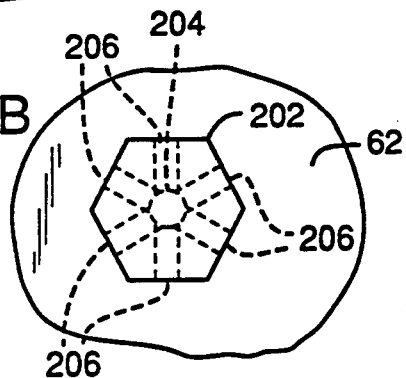
FIG. 4B is a detailed plan view of the hexagonal member of FIG. 4A.

FIGS. 2, 3, 4A and 4B show details of the specifically illustrated gas and liquid dispersion mechanism. Referring to FIG. 2, a four-foot diameter reactor has a first transverse plate 61 positioned beneath the second transverse plate 62. The first transverse plate 61 is approximately two feet in diameter and is positioned inside housing 12 downstream from inlet 16. Transverse plate 61 serves to cause the incoming stream of liquid and gases to flow in a radial pattern transverse to the longitudinal axis of the reactor. After passing around transverse plate 61, the stream encounters transverse plate 62 which defines a plurality of apertures 204 therethrough (one being numbered in FIG. 2 and in FIG. 4A). Each of these apertures is capped with a hexagonal member 202 which is provided with a plurality of radially oriented apertures 206 (FIGS. 4A and 4B). The mixture of gases and liquid, in order to pass through transverse plate 62, must pass through aperture 204 and through apertures 206 in each hexagonal member 202, thereby becoming substantially evenly distributed across the diameter of housing 12 as the mixture passes through transverse plate 62. Between the substrate bed 20 and the transverse plate 62 is a layer of gravel 212 which further serves to distribute the flow of the liquid and gases evenly across the diameter of housing 12. This gravel also separates apertures 206 from the bed material and thereby minimizes possible clogging of the apertures 206 with the bed material. Of course, other suitable flow distribution mechanisms may also be used, such as other types of baffle mechanisms and injecting the gases through multiple ports arranged at various locations along the length and diameter of the reactor (details not shown).

A plurality of valved sampling ports 64 (FIG. 1) may be positioned along the length of the housing 12 for use in sampling the aqueous mixture at various points along the length of the bed 20. The sampling ports 64 may also be used for monitoring the biodegradation of organic compounds in the mixture which occurs at various locations in the bed.

Replacement or cleaning of the bed, or of portions of the bed, is performed when the bed, or portions thereof, become clogged with solids or biomass. Frequency of bed cleaning or replacement is minimized when wastewater having a low solids content and/or low concentration of total organic carbon (TOC) or biochemical oxygen demand (BOD) is being passed through the bed, or when the transit time of the liquid through the bed is shortened so that dehalogenation is favored over BOD removal. As described below in connection with FIG. 10, bed clogging can be minimized by performing optional preliminary solids-removal and BOD-reduction steps on the wastewater before the water enters the bioreactor. In general, to reduce the need for bed cleaning, it is desirable to minimize the mass of TOC removed by the microorganisms on bed 20. More specifically, it is preferable that the microorganisms reduce the TOC of the aqueous mixture by a controlled minimum as the aqueous mixture passes through the bed.

In the FIG. 1 form of the invention, an optional bed-cleaning mechanism is provided. This illustrated cleaning mechanism includes a source of pressurized water 70 which is coupled through a valve 72 and a conduit 74 to plural nozzles (not shown) located at the base of bed 20. During a bed cleaning operation, the source of wastewater 50 is shut off at valve 52. In addition, the supply of air and methane gases from respective sources 22 and 34 are shut off from the bed 20 at valve 30, and valve 72 is opened to direct pressurized water to the base of the bed. The flow of pressurized water expands the bed into an upper region 76 of the chamber 14 as indicated by dashed lines 78. The rate of water flow through the expanded bed is more rapid, thereby agitating the bed particles and stripping the accumulated deposits off the bed material. The bed may then be reacclimated as required, and treatment of wastewater resumed. A backup reactor may be coupled to conduit 60 while the primary reactor is being cleaned, thus precluding any interruption of flow of wastewater from the source 50.

Liquid passing through the bed 20 leaves the chamber 14 at outlet 18. In addition, residual gases also exit from the bed 20 by way of this outlet. These residual gases include left-over air or oxygen and low-molecular-weight alkane gases which are supplied to the bed but not used by the microorganisms. In addition, the residual gases may also include any metabolic gases generated but not used during the biodegradation process. Typically, an excess amount of low-molecular-weight alkane and air or oxygen is provided to ensure optimal co-metabolism of the contaminants by the microorganisms. For example, volume ratios of liquid to air to methane of from 1/11.4/0.62 to 1/72.3/4.0 are typically suitable at standard conditions. After setting up a biological reactor near a source of contaminated water, these ratios may be adjusted as required to enhance the biodegradation of specific organic contaminants by the biological reactor 10 and to maximally reduce the level of organic contaminants in the water.

Because the bioreactor of the present invention depends upon aerobic microbial metabolism to achieve biodegradation of waste organic compounds flowing therethrough, it is important to set the flow rate and oxygen concentration of the oxygen-containing gas entering the bioreactor so as to ensure maintenance of aerobic conditions throughout the bed. Further, testing has shown that the concentration of methane or other low-molecular-weight alkane throughout the bed should be maintained at 0.1 mg/L or higher to ensure satisfactory co-metabolism by the microorganisms of the organic compounds flowing through the bed.

Referring further to FIG. 1, outlet 18 is connected to a conventional liquid gas separator 80 for separating the residual gases from the treated aqueous mixture. The treated mixture is delivered from separator 80 through a drain line 82 as indicated by arrow 84. Air ports 86 in the separator 80 are provided to admit additional air to the separator.

Oxygen and low-molecular-weight alkanes can form potentially explosive mixtures. For example, methane gas at a concentration greater than 5.5% in air at room temperature and pressure is explosive. A conventional explosion vent 88 is provided in the roof of the housing 12 to release excess pressure from the biological reactor in the event of a flare or explosion. To further reduce the risk of flare or explosion, a means is provided for supplying a dilution gas to the residual gases leaving the separator 80. That is, these residual gases flow upwardly through a stack 90 and exit, as indicated by arrows 92, from an opening 94 at the top of the stack. A dilution-gas supply inlet 96 is provided in the stack 90 below the stack opening 94. A dilution gas, such as air, is blown by a fan 98 through a conduit 100 and to the dilution gas supply inlet 96, as indicated by arrows 102 in FIG. 1. The dilution gas is used to maintain the concentration of exhausted low-molecular-weight alkane below the lower explosive limit of the particular alkane.

Figure 5:
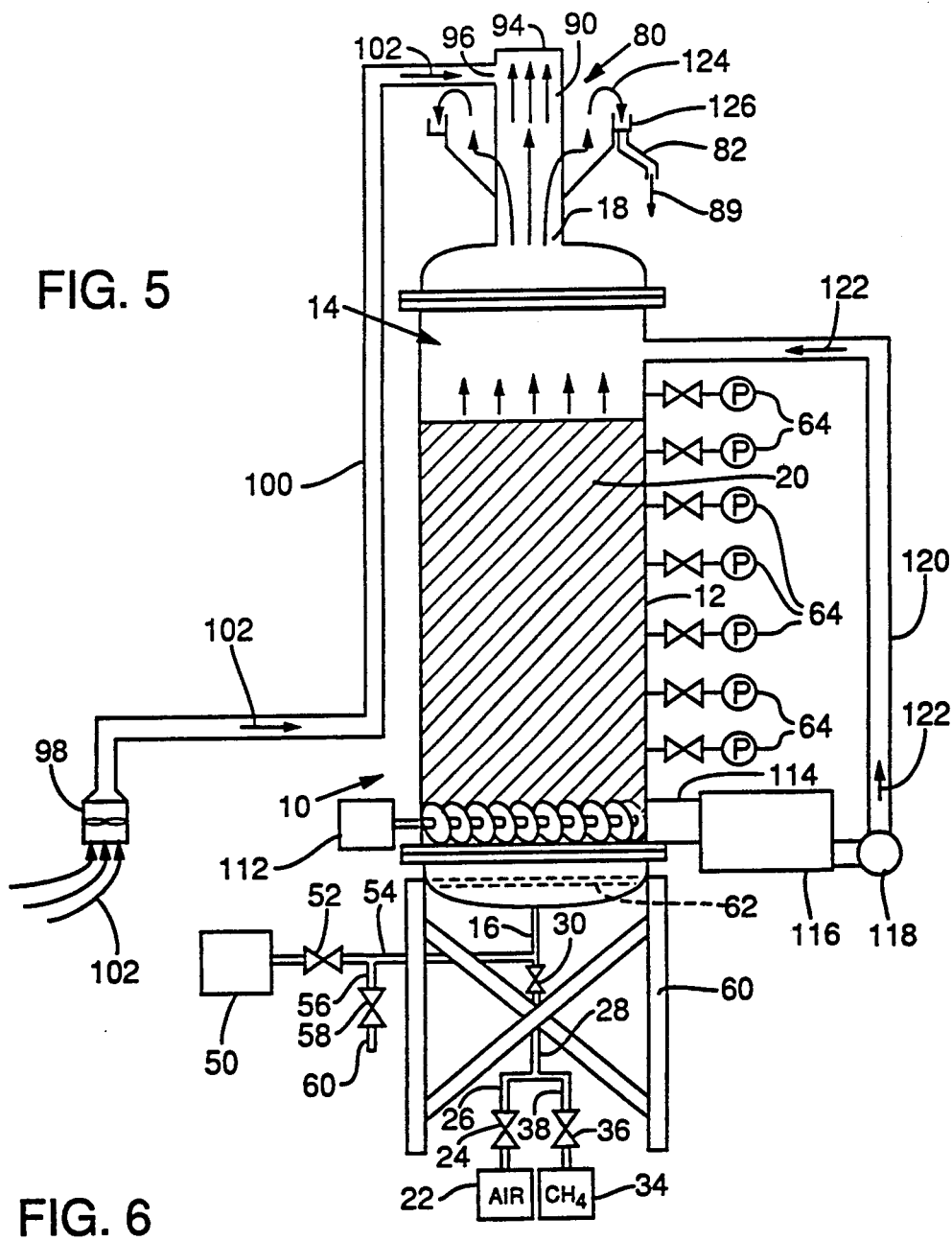
FIG. 5 is a schematic front elevational view of another form of biological reactor in accordance with the invention.

Except for its use of a different optional bed cleaning mechanism and a slightly different liquid/residual gas separator 80, the FIG. 5 form of biological reactor 10 is identical to the FIG. 1 form of reactor. Therefore, like elements have been assigned like numbers in FIG. 2 and will not be discussed in detail.

The FIG. 5 bed cleaning mechanism includes a feed screw 110 which is selectively driven by a motor 112 to move substrate bed particles from a lower region of the bed through a conduit 114 and into a cleaning apparatus 116. Typically, the cleaning apparatus 116 includes plural nozzles (not shown) for washing the bed material and for agitating this material during washing. During cleaning, solids detached from the bed particles are separated and flushed away. A pump 118 returns the cleaned bed material by way of a conduit 120 to an upper region of the bed 20, as indicated by arrows 122.

In the FIG. 5 form of the invention, the wastewater from source 50, and gases from sources 22 and 34 are supplied to a lower portion of the bed and flow upwardly through the bed. As described below in connection with FIG. 8, in many applications the bulk of the contaminant removal occurs in lower regions of the bed. Therefore, by removing and cleaning the bed material from these lower regions, the material which is most susceptible to clogging is removed and cleaned. As cleaned bed material is returned to the top of the bed, the entire bed shifts downward to fill the void left by rotation of the feed screw 110. In addition, when cleaned bed material is returned to the upper region of the bed, the microorganisms will re-colonize this cleaned bed material very quickly, long before the material has returned to lower portions of the bed where most of the contaminant removal occurs.

The FIG. 5 form of liquid/gas separator 80 is similar to the FIG. 1 liquid/gas separator. However, in FIG. 5 the liquid is separated, as indicated by arrows 124, from the residual gases and collected in a trough 126. Liquid is removed from the trough 126 via the drain line 82, as indicated by arrow 84.

Figure 6:
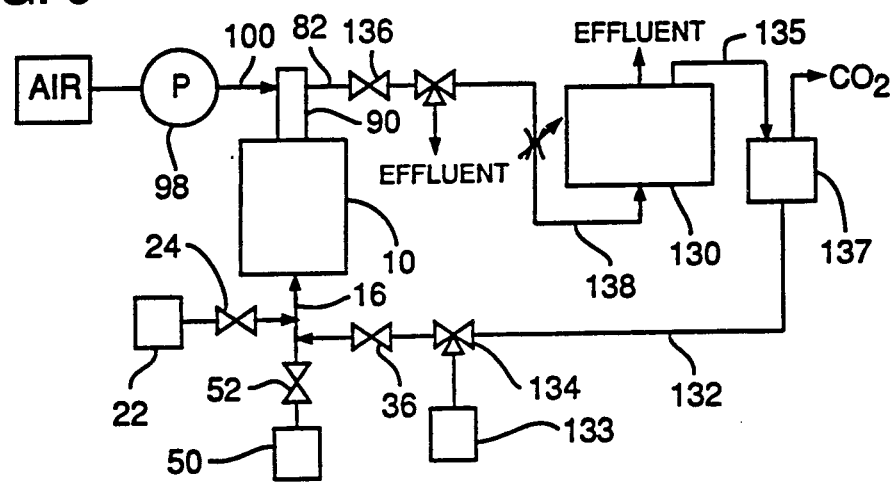
FIG. 6 illustrates a primary biological reactor in accordance with the present invention with a secondary reactor containing methanogenic microorganisms, the secondary reactor being utilized for generating and supplying at least a portion of the methane gas used by the primary biological reactor.

FIG. 6 is a block diagram showing how an aerobic biological reactor 10 similar to the FIGS. 1 and 5 forms can be connected in series with a secondary anaerobic methanogenic reactor 130. The anaerobic methanogenic reactor is used to supply methane to a population enriched with methanotrophic microorganisms in the bed of the reactor 10. In FIG. 6, like elements to those of FIGS. 1 and 5 have been assigned like numbers and will not be discussed in detail.

Structurally, the secondary reactor 130 may be similar to reactor 10, although it is not supplied with oxygen or low-molecular-weight alkane extraneous as a carbon and energy source. The reactor 130 contains a substrate bed on which methanogenic microorganisms are supported. Methanogenic microorganisms naturally inhabit anaerobic benthal sediments of both natural aquatic environments and man-made waste treatment lagoons. Methanogens produce methane and carbon dioxide via biodegradation of organic substances. The methane rises to higher sedimentary layers populated by methanotrophs which metabolize the methane. In FIG. 6, the methane gas from secondary reactor 130 is delivered from this secondary reactor through a conduit 135 to a carbon-dioxide separator 137. The separated methane then passes through a conduit 132, through a valve 134, through the valve 36, and to the inlet 16 of the biological reactor 10. Thus, reactor 130 comprises a source of methane for the primary reactor 10.

The reactor 130 may be sized sufficiently to provide all of the methane required by the primary reactor 10. The capacity of reactor 130 to supply the methane requirements of reactor 10 will, in this specific configuration, depend upon the BOD of the wastewater effluent from the primary reactor 10. Alternatively, a backup methane source 133, such as a natural gas pipeline, may be coupled through the valve 134 to the conduit 132 to supply methane to reactor 10 in the event that reactor 130 produces an insufficient supply or is removed from service.

Although the methanogenic microorganisms in reactor 130 may be supplied with any suitable source of carbon and energy, it is particularly advantageous to use some of the treated water from the primary reactor 10 as the carbon and energy source for the secondary reactor 130. As shown in FIG. 6, a portion of the treated water from the primary reactor 10 is passed through a valve 136 and a conduit 138 to the methanogenic reactor 130. Any residual organic compounds and other dissolved or suspended metabolic by-products in the treated water comprise the carbon and energy source for the methanogenic microorganisms in the secondary reactor 130. Operating parameters of the primary reactor 10, such as liquid detention time, may be adjusted such that the primary reactor 10 predominantly performs dehalogenation, thereby allowing non-halogenated organic compounds to pass through the reactor and be available as a carbon and energy source for the methanogens in the secondary reactor 130.

In some cases, it may be necessary to supply the methanogens with additional carbonaceous material. For example, a portion of the benthic layer from an upstream biopond may be added to the treated water from the primary reactor 10 before the water enters the methanogenic reactor 130 (details not shown). Since methanogens normally inhabit benthic sediments where the organisms facilitate decomposition of dead biomass, it may be necessary to fortify the liquid flowing through the bed of methanogens in the secondary reactor 130 with such benthic material for optional methane production. Such fortification may be particularly important if the primary biological reactor 10 has been especially effective in removing total organic carbon from the liquid passing therethrough.

Because bioponds and landfills also product appreciable quantities of methane, a biopond, landfill, or other methane source upstream of the primary reactor 10 may also be used to generate or supply methane for the primary reactor. To collect the methane, a cover can be placed over the biopond or landfill, with a means included for separating other gases (principally carbon dioxide) from the methane before routing the methane to the primary reactor.

Figure 12:
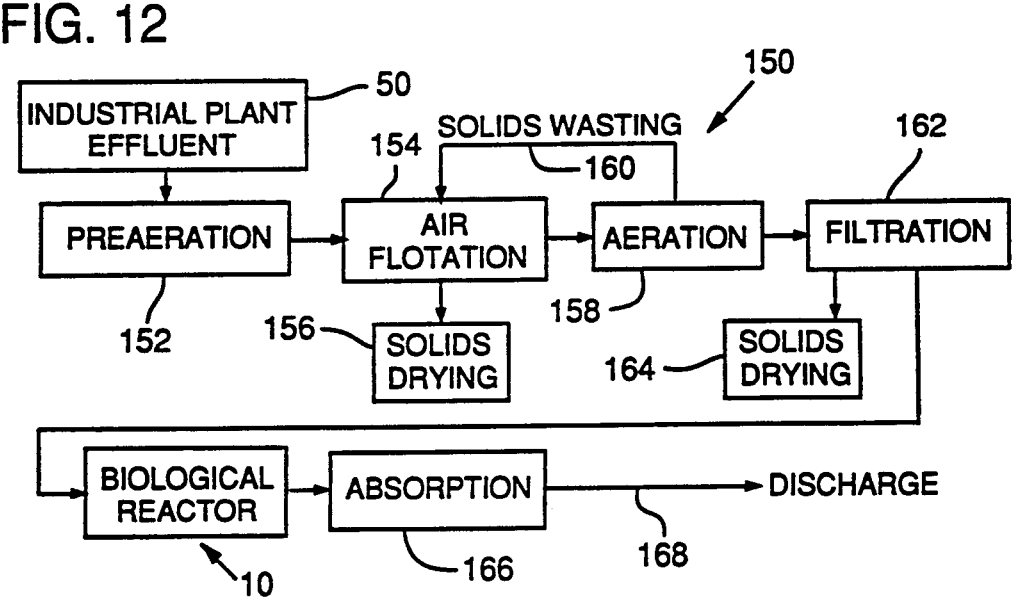
FIG. 12 is a schematic block diagram of one form of an overall wastewater treatment system which includes a biological reactor in accordance with the present invention.

With reference to FIG. 12, a pretreatment or solids-removal subsystem 150 may be used in conjunction with one or more of the biological reactors 10. Typically, the pretreatment subsystem receives industrial plant wastewater effluent, as indicated at 50, or contaminated water from some other source. The subsystem 150 is designed to remove solids and a portion of the organic carbon from the contaminated water prior to delivering the contaminated water to the biological reactor 10. By removing these materials, the risk of clogging the biological reactor 10 with biomass is substantially reduced.

Although other subsystems are, of course, suitable, including bioponds or lagoons, subsystem 150 includes conventional components such as a preaeration tank 152, in which the wastewater is aerated to promote initial chemical and biological breakdown of the contaminants. The preaeration stage is followed by an air flotation stage 154. At the stage 154, some solids are removed from the wastewater and may be dried, as indicated at 156. A second aeration stage 158 follows the air flotation stage 154. Solids from the second aeration stage 158 are fed back to the air flotation stage 154 for removal. Remaining solids may be removed from the wastewater at a filtration stage 162 which follows the second aeration stage. These removed solids may be dried at a solids drying stage 164. The pretreated contaminated water is then fed to the biological reactor 10. If necessary, the treated water from biological reactor 10 may be polished in a final adsorption stage 166, with the treated water being discharged through a conduit 168.

The following examples are presented to illustrate the invention, but the invention is not to be considered as limited thereto.

EXAMPLE 1

In this first example, an inoculum containing a mixed population of methylotrophic and various other heterotrophic microorganisms was obtained from an aerobic biopond used to treat waste liquid from a kraft paper mill. In particular, the inoculum was obtained from a wastewater pond at a Weyerhaeuser Company mill in Everett, Washington. The inoculum was used to colonize the substrate bed 20 of the FIG. 1 form of biological reactor 10 as explained in greater detail above in connection with FIG. 1. The specific bed 20 used in this example comprised a packed volume of spent granular activated carbon having little residual adsorptive capacity. The housing 12 in this example was four feet in diameter and nine feet high, and was packed to near capacity with the activated carbon particles. The granules had a size ranging from $8 \times 30$ mesh to $12 \times 40$ mesh. In this example, methane was supplied to the bed 20 as natural gas from a pipeline source 34. Air was used as the oxygen source.

After full colonization was achieved in the manner previously described in connection with FIG. 1, the liquid inlet of the housing was hydraulically coupled to the effluent stream of a plant applying pentachlorophenol to wood as a preservative. The liquid flow rate through the reactor was started at one gal/min, then increased respectively to two and three gal/min at later times. Also, the methane and air flow rates were typically set at 0.25 and 9 standard cubic feet per minute, respectively. Performance data were collected, as discussed below, over a substantial period of time (90 days). Also, the pH was maintained throughout the bed in the range of from about 6.0 to 8.0.

Figure 7:
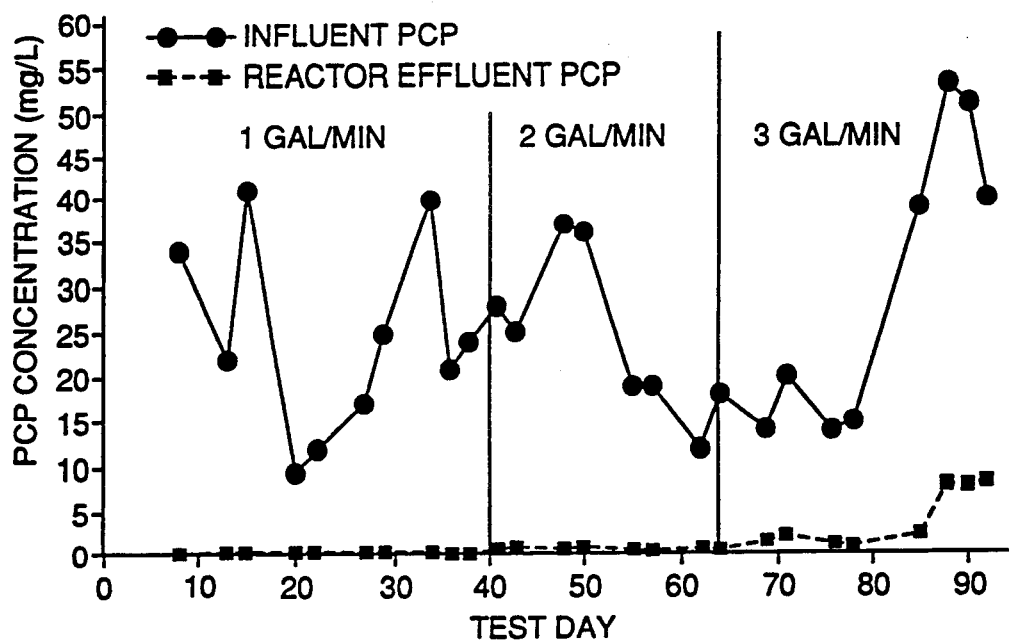
FIG. 7 is a graph illustrating the reduction of the concentration of pentachlorophenol achieved when a biological reactor of the invention was in use coupled to a wastewater effluent line of a wood treatment plant.

Referring to FIG. 7, the liquid flow rate through the reactor was begun at one gal/min and maintained at this rate until day 40 when the flow rate was increased to two gal/min. The flow rate was increased to three gal/min at day 63. The concentration of pentachlorophenol in the aqueous mixture flowing into the bed (influent PCP) fluctuated widely and ranged from 9.5-53 mg/L, depending upon the particular day. The concentration of pentachlorophenol exiting the bed (reactor effluent PCP) was consistently reduced to less than 1 mg/L at one gal/min flow rates, to less than 2 mg/L at two gal/min flow rate, and to less than 8 mg/L at three gal/min flow rate, yielding a mean PCP reduction upon passing through the reactor of 99.9%, 99.2% and 87.5% at one, two and three gal/min, respectively. Pentachlorophenol biodegradation did not occur via adsorption on the substrate bed because the carbon granules comprising the bed were "spent" to the extent that they would be unable to adsorb organic compounds of levels being treated in the reactor. FIG. 7 also shows that the effluent PCP concentration remains very stable, even against appreciable daily variations in influent PCP concentration, indicating the performance-buffering effect which is apparently due to the use of the spent activated carbon substrate.

Because the reactor of FIG. 1 used in this example was used out of doors, and because the weather became colder as the tests continued, FIG. 7 shows a decrease in reactor efficiency after day 80 that correlated with a progressively colder ambient temperature (temperature data not shown). Other testing indicated that the reactor operated most efficiently at temperatures between 25° and 35° C. Lower reactor operating temperatures resulted in operation of the biological reactor at a reduced efficiency, with efficiency generally dropping off with falling temperature.

The influent wastewater flowing into the reactor of this example had a methanol concentration of approximately 7-9 mg/L. The effluent water had a methanol concentration of 3-5 mg/L, at a flow rate of one gal/min. These data showing the utilization of methanol in the reactor are consistent with the presence of methylotrophic organisms on the substrate bed.

Figure 8:
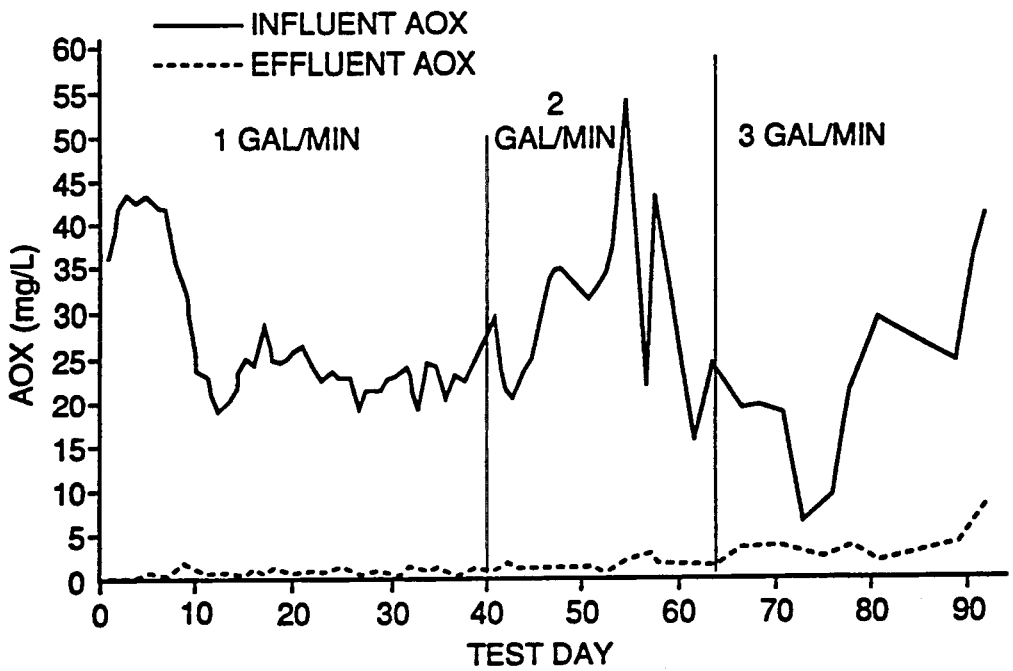
FIG. 8 is a graph illustrating the reduction in soluble absorbable organic halide (AOX) concentration achieved when a biological reactor of the invention was in use coupled to a wastewater effluent line of a wood treatment plant.

Referring to FIG. 8, the concentration of adsorbable organic halide (AOX) in the aqueous mixture flowing into the bed (influent AOX) ranged from 6 to 54 mg/L, depending upon the particular day. At one gal/min flow rate through the bed (days 1-40), the mean AOX reduction was 96.7%. At two gal/min flow rate (days 41-63), the mean AOX reduction was 95.1%. At three gal/min flow rate (day 64 to end), the mean AOX reduction was 82.7%. In all cases, effluent AOX was lower than influent AOX, indicating that the microorganisms on the substrate bed effectively removed at least most of the AOX from the aqueous mixture. Such a decrease in AOX coupled with a corresponding increase in inorganic halide (IX) (data not shown) indicate that halogen atoms (here chlorine atoms on pentachlorophenol molecules) are being removed from the organic molecules in the aqueous mixture. In other words, the microorganisms in the bed are dehalogenating the organic compounds in the mixture as the mixture passes through the bed. The progressive increase in concentration of effluent AOX, especially toward the end of the 90-day experiment, was due to a general decrease in reactor temperature (the reactor was located out of doors where the average ambient temperature decreased as the experiment continued into winter.

Figure 9:
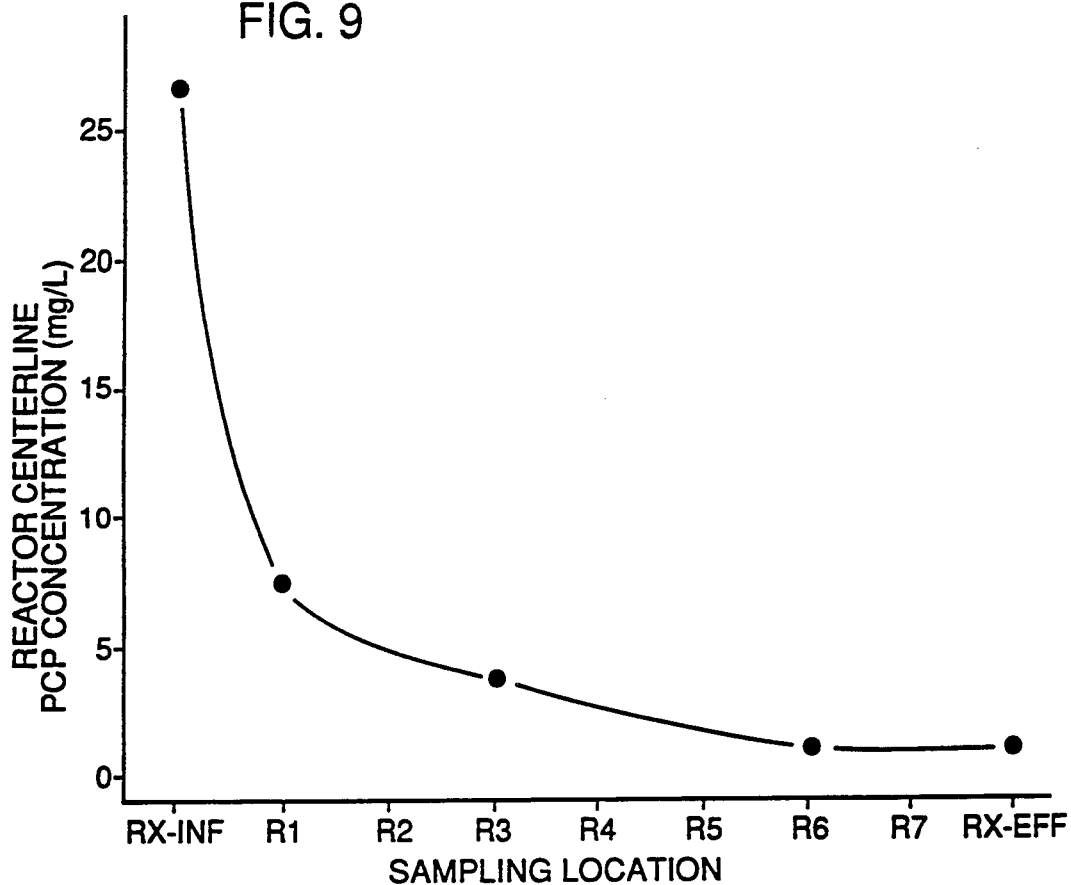
FIG. 9 is a graph illustrating the concentration of pentachlorophenol in a biological reactor of the invention, measured at various points along the longitudinal axis of the reactor from the wastewater receiving portion of the reactor, while the biological reactor was in use coupled to a wastewater effluent line of a wood treatment plant.

In FIG. 9, it can be seen that the pentachlorophenol concentration was reduced along the axis of the reactor from the liquid inlet to the various sampling ports 64 (FIG. 1). This data reveals that most of the biological activity occurred in lower portions of the bed. This indicates that the total capacity of the biological reactor 10 of this example is not required to remove up to 28 mg/L pentachlorophenol in an aqueous liquid mixture flowing through the bed at 3 gal/min.

Figure 10:
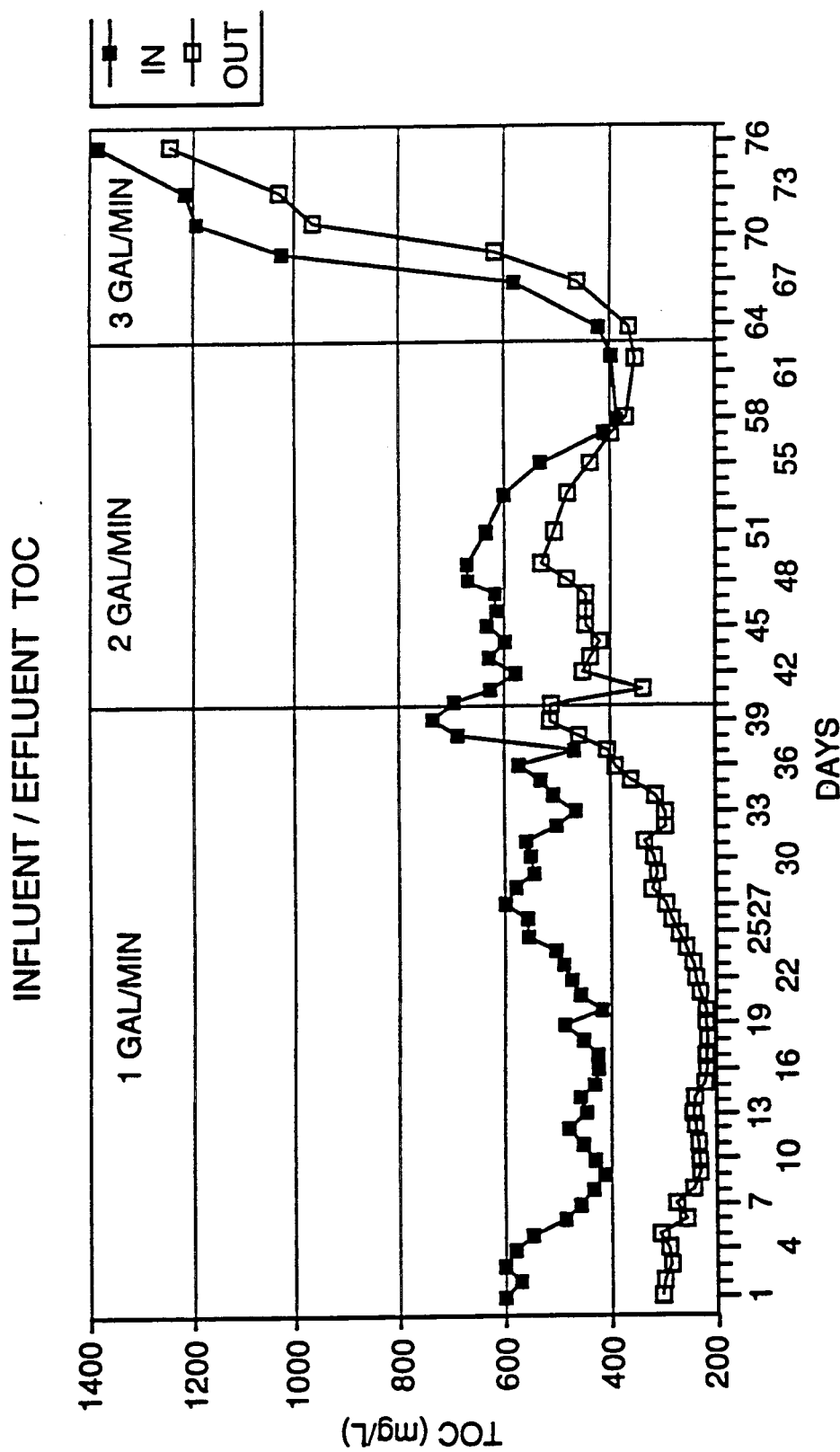
FIG. 10 is a graph illustrating changes in the concentrations of total organic carbon of the aqueous mixture passing through a biological reactor of the invention when the reactor was in use coupled to a wastewater effluent line of a wood treatment plant.

The bioreactor of this example also reduced the total organic carbon concentration (TOC) of the aqueous mixture as it passed through the bed. In FIG. 10, the concentration of TOC of the influent aqueous mixture ranged from approximately 400 to approximately 1400 mg/L over a 76-day test. The TOC concentration of the aqueous liquid exiting the bioreactor was consistently lower. It is desirable that the TOC of the liquid passing through the bed remain either substantially constant or decrease slightly. Too great a decrease greater than the approximately 50-percent maximum decrease seen in FIG. 10) can lead to excessive biomass accumulation in the bed, which can clog the bed and necessitate replacement or cleaning of the bed. The observed decrease in TOC indicated that some biodegradation of the organic compounds present in the aqueous mixture occurred while the liquid passed through the bed.

Figure 11:
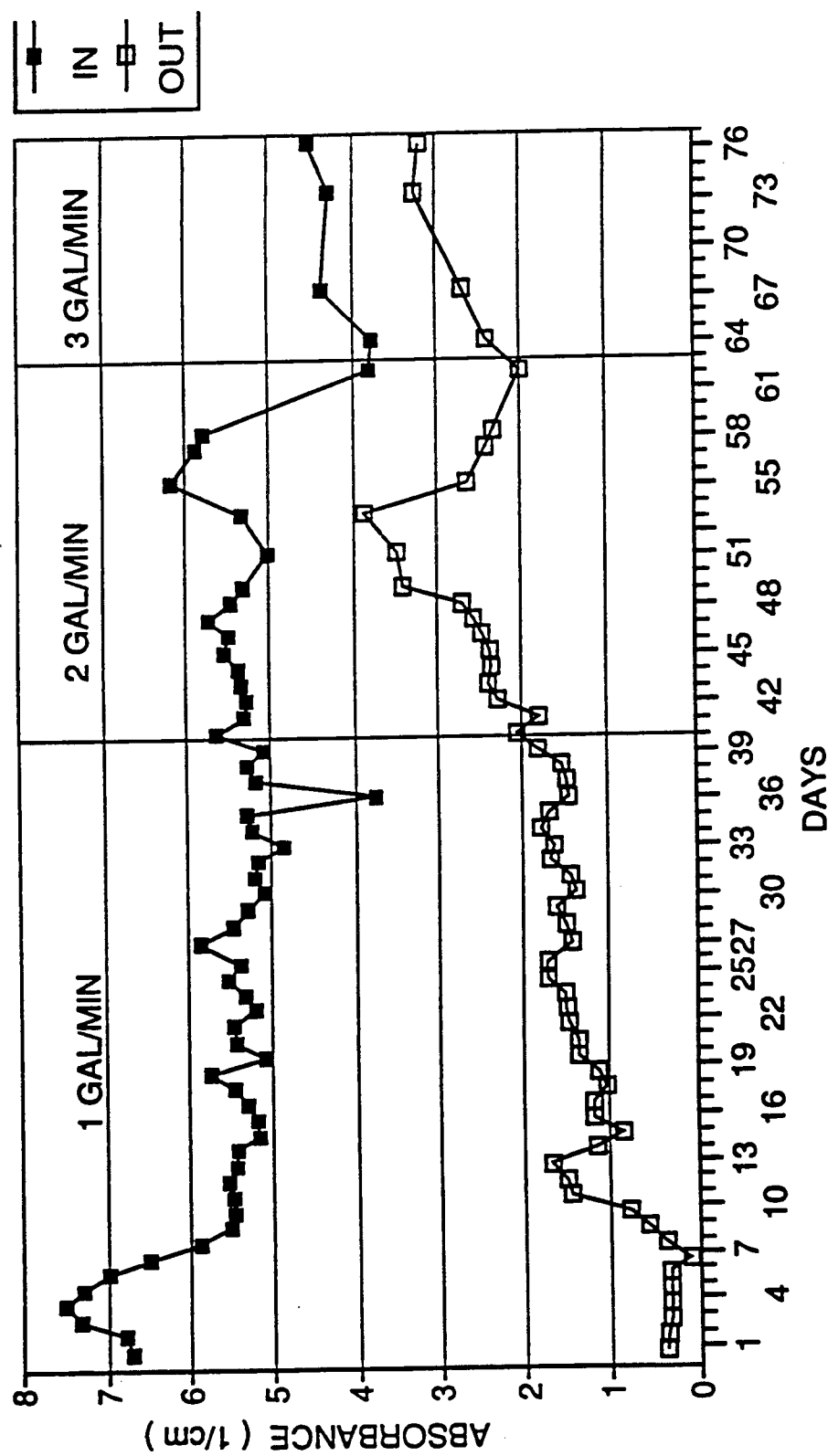
FIG. 11 is a graph illustrating the decrease in the ultraviolet absorption at 254 nanometers of an aqueous mixture as the mixture passed through a biological reactor of the invention when the reactor was in use coupled to a wastewater effluent line of a wood treatment plant.

FIG. 11 shows the results of an experiment conducted over 76 days, in which absorbance at 254 nm ($A_{254}$) of the aqueous liquid mixture both entering and exiting the bioreactor was monitored. As can be seen, the effluent $A_{254}$ consistently substantially lower than influent. Because $A_{254}$ is a "signature" of aromatic compounds, a decrease in $A_{254}$ indicates that the methanotrophic microorganisms are breaking the benzene ring moiety of the pentachlorophenol in the aqueous mixture as it passes through the bed.

Although dioxin tests are difficult and expensive to obtain, Table I shows the average results of one series of tests in which influent and effluent concentrations of various dioxins and dibenzofurans were determined. The influent and effluent samples were tested for each of these compounds and the results were then averaged. The tetra- through hexa-homologs of both compounds were undetectable in either the influent or effluent streams. The hepta- and octa-homologs were detectable. For some unexplained reason, perhaps due to sampling errors, one measurement of octa-homologs of dioxin in reactor influent and effluent indicated that the concentration of this compound increased slightly across the reactor (but was essentially the same concentration within experimental error). However, on average a substantial decrease in octa-homologs of dioxin was noted. Other than this one exception, all other cases of the hepta- and octa-homologs, passing the liquid through the bioreactor of the present invention resulted in a substantial decrease in concentration of the homolog. Hence, the bioreactor of the present invention can biodegrade dioxin compounds. It is expected that biodegradation of tetra- through hexa-homologs of these compounds, if present in this influent to the reactor 10, would also be achieved.

TABLE I

| Compound Tested | Average Influent | Average Effluent | Average Decrease | Percent Degraded |
|---|---|---|---|---|
| Dioxin | | | | |
| hepta-Cl | 11.4 ppt | 9.2 ppt | 2.2 ppt | 20% |
| octa-Cl | 70.4 ppt | 49.6 ppt | 20.8 ppt | 30% |

TABLE I-continued

| Compound Tested | Average Influent | Average Effluent | Average Decrease | Percent Degraded |
|---|---|---|---|---|
| Dibenzofuran | | | | |
| hepta-Cl | 38.6 ppt | 13.0 ppt | 25.6 ppt | 65% |
| octa-Cl | 42.6 ppt | 18.6 ppt | 24.0 ppt | 55% |

In the above table, ppt = parts per trillion.

EXAMPLE 2

The apparatus of this example is the same as in Example 1 except that, after the reactor had been in service for 128 days, with natural gas, air, and the aqueous liquid mixture containing pentachlorophenol flowing through the bed as described in Example 1, the natural gas supply was turned off. Air and the aqueous liquid mixture were allowed to continue flowing uninterrupted through the reactor, the aqueous mixture flowing at 1 gal/min. The concentrations of pentachlorophenol in the reactor influent and effluent streams were then monitored. It was found that, when the supply of methane to the microorganisms in the bed was turned off, the percent reduction in PCP concentration of the aqueous mixture as it flowed through the bed dropped from approximately 90 percent to approximately 75 percent at a given operating temperature. These results indicate that, while the substrate bed contains methanotrophic microorganisms thereon, the bed also contains other methylotrophic as well as other heterotrophic microorganisms that do not require a source of methane to effect biodegradation of the PCP. Because the aqueous liquid mixture flowing into the bed contained approximately 7-8 mg/L methanol, and the effluent from the reactor contained less than 5 mg/L methanol, it was concluded that methylotrophs in the bed utilized the methanol as a carbon and energy source for co-metabolism, enabling the reactor to continue functioning even in the absence of methane. Also, while methane is the preferred carbon and energy source for the microorganisms colonized throughout the bed, the reactor will perform satisfactorily with sufficient methanol or other carbon and energy source to permit co-metabolic activity to continue.

EXAMPLE 3

It was discovered while testing a laboratory-scale version (1-inch diameter column, flow direction upward) of the FIG. 1 embodiment that either methane or propane gas flowing through the bed 20 as a carbon and energy source for the microbes is effective in enabling the microbes to biodegrade various organic compounds. Results of such tests are shown in Table II, where biodegradation of a PCP-laden aqueous mixture was evidenced by substantial decreases in the concentration of total adsorbable organic halide (AOX) in the effluent from the reactor, relative to the AOX concentration of the influent. As shown in Table II, flowing propane through the bed was nearly, but not quite, as effective as flowing methane therethrough. Therefore, while methane gas is preferred, other low-molecular-weight alkanes will also yield satisfactory reactor performance. These results also indicate that the microbial population in the bed was comprised of at least both methanotrophic and other methylotrophic species.

TABLE II

| | | Effluent AOX (mg/L) | | |
|---|---|---|---|---|
| Day | Influent AOX (mg/L) | Propane Inoculum Source 1 | Methane Inoculum Source 1 | Methane Inoculum Source 2 |
| 1 | Start | | | |
| 7 | 11.552 | 0.093 (99.2%) | ND (100%) | ND (100%) |
| 12 | 12.848 | 1.661 (87.1%) | 1.080 (91.6%) | 1.170 (90.9%) |
| 14 | 8.794 | 1.575 (82.1%) | 1.025 (88.3%) | 1.075 (87.8%) |
| 26 | 16.046 | 1.490 (90.7%) | 0.740 (95.4%) | 0.400 (97.5%) |

Table II also shows that inocula obtained from two different sources (intermediate layers from two different aerobic waste treatment lagoons treating effluent from different kraft pulp mills) are approximately equally effective in reducing the concentration of AOX of the same aqueous mixture when methane is also flowed through the bed. In the above table, ND means not detected. Also, the percentages refer to the percentage reduction of AOX in the effluent.

Having illustrated and described the principles of our invention with reference to several preferred embodiments, it should be apparent to those of ordinary skill in the art that the invention may be modified in arrangement and detail without departing from such principles. We claim as our invention all such modifications as come within the true spirit and scope of the following claims.

We claim:

1. A method for dehalogenating and further biodegrading organic compounds present in an aqueous liquid mixture to at least partially reduce the concentrations of the organic compounds in the mixture, the method comprising:

supporting a mixed population of aerobic microorganisms on a substrate bed configured to allow liquid to flow therethrough with the liquid contacting the microorganisms;

passing the aqueous mixture containing halogenated organic compounds through the bed such that the microorganisms in at least a portion of the bed dehalogenate and metabolize the organic compounds in the mixture as the liquid flows through the bed;

maintaining a concentration of oxygen substantially throughout at least a portion of the bed which is sufficient to provide aerobic conditions in at least a portion of the bed, as the aqueous mixture flows through the bed; and maintaining a concentration throughout the bed of a carbon and energy source for microorganisms on the bed, whereby the microorganisms dehalogenate and further biodegrade the organic compounds in the aqueous mixture via a co-metabolic process as the liquid flows through the bed.

2. The method of claim 1 wherein the aerobic microorganisms are a mixed population including at least one species of methylotrophic microorganisms, and in which the carbon and energy source is any of the group of saturated alkanes having one to four carbon atoms.

3. The method of claim 2 wherein the low-molecular-weight alkane comprises methane and the microorganisms include methanotrophic microorganisms.

4. The method of claim 2 wherein the concentration of the low-molecular-weight alkane throughout the bed is at least 0.1 mg/L.

5. The method of claim 1 wherein the carbon and energy source comprises methanol.

6. A method for dehalogenating and further biodegrading organic compounds present in an aqueous mixture to at least partially remove the concentrations of the organic compounds in the liquid, the method comprising:

supporting a population of methylotrophic microorganisms on a substrate bed comprised substantially of manufactured materials;

flowing a carbon and energy source for the microorganisms through the bed;

flowing a gas consisting at least partially of oxygen through the bed;

passing the aqueous liquid mixture containing halogenated organic compounds through the bed with the carbon and energy source and the gas consisting at least partially of oxygen such that the microorganisms dehalogenate and metabolize the organic compounds in the aqueous mixture as the liquid passes through the bed.

7. The method of claim 6 including the step of decreasing the biochemical oxygen demand of the aqueous liquid mixture prior to passing the aqueous liquid mixture through the bed.

8. The method of claim 6 including the step of removing solids from the aqueous mixture prior to passing the aqueous liquid mixture through the bed.

9. The method of claim 6 including the step of maintaining the biochemical oxygen demand of the aqueous mixture passing through the bed at a substantially constant level.

10. The method of claim 6 wherein the aqueous liquid mixture undergoes a controlled minimum decrease in total organic carbon as it passes through the bed.

11. The method of claim 6 including the step of continuously passing the aqueous liquid mixture through the bed.

12. The method of claim 6 wherein the substrate bed is comprised of a solid material in particulate form.

13. The method of claim 12 wherein the substrate bed is of particles having a large specific surface area.

14. The method of claim 6 wherein the substrate bed is comprised of a solid material having a capacity to adsorb organic compounds.

15. The method of claim 14 wherein the substrate bed is preloaded with organic compounds during colonization of the bed with the microorganisms.

16. The method of claim 6 wherein the substrate bed is comprised substantially of granules of activated carbon.

17. The method of claim 6 including the preliminary steps of obtaining an inoculum of microorganisms from a native population of such microorganisms occupying a depth zone between an underlying anaerobic benthal layer and an overlying aerobic layer of a pond having such layers, introducing the inoculum into the bed and colonizing the bed with the inoculum.

18. The method of claim 6 wherein the organic compounds in the aqueous liquid mixture include halogenated and non-halogenated alkanes, alkenes, and aromatics.

19. The method of claim 6 wherein the organic compounds in the aqueous mixture include pentachlorophenol and wherein there is a substantial decrease in the concentration of pentachlorophenol in the aqueous liquid mixture as it passes through the bed.

20. The method of claim 6 wherein the organic compounds in the aqueous mixture include dioxin and at least one other organic compound and wherein dehalogenation of such one other organic compound is performed in the presence of the dioxin and there is a decrease in the concentration of dioxin in the aqueous liquid mixture as it passes through the bed.

21. The method of claim 6 wherein the organic compounds in the aqueous mixture include soluble adsorbable organic halide and wherein there is a substantial decrease in the concentration of soluble adsorbable organic halide in the aqueous liquid mixture as it passes through the bed.

22. The method of claim 6 wherein the organic compounds in the aqueous mixture include aromatic hydrocarbons and wherein there is a substantial decrease in ultraviolet absorption at 254 nanometers of the aqueous liquid as the aqueous liquid mixture passes through the bed.

23. The method of claim 6 wherein the organic compounds in the mixture include furan and at least one other organic compound and wherein dehalogenation of such one other organic compound is performed in the presence of furan and there is a decrease in the concentration of furan in the aqueous liquid mixture as it passes through the bed.

* * * * *

UNITED STATES PATENT AND TRADEMARK OFFICE
CERTIFICATE OF CORRECTION

PATENT NO. : 5,057,221
DATED : October 15, 1991
INVENTOR(S) : Bryant et al.

It is certified that error appears in the above-identified patent and that said Letters Patent is hereby corrected as shown below: On the title page: Item [56]

U.S. Patent Documents:

The following U.S. Patent documents are missing (filed and should be added:

```
--4,348,476   9/1982   Hou     435/123--
--4,904,600   2/1990   Ramp    435/299--.
```

Foreign Patent Documents:

The following Foreign Patent documents are missing and should be added:

```
--0025309   3/1881    Europe--
--0322749   7/1989    Europe--
--2167085   5/1986    U.K.--
--3715952   11/1988   German Offenlegungs--.
```

Other Publications:

column 2, "45:1038-1044" should read --46:1038-1044--.

column 1, "48:46-53" should read --49:46-53--.

column 1, "48:242-243" should read --49:242-243--.

column 2, "(TCDD),a *Abstr.*" should read --(TCDD) *Abstr.*--.

UNITED STATES PATENT AND TRADEMARK OFFICE
CERTIFICATE OF CORRECTION

PATENT NO. : 5,057,221
DATED : October 15, 1991
INVENTOR(S) : Bryant et al.

It is certified that error appears in the above-identified patent and that said Letters Patent is hereby corrected as shown below:

Abstract:

column 2, line 7,) "particlate", should read --particulate--.

Column 10, line 40 "higher Also,", should read --higher. Also,--.

Column 18, line 19 (page 34, line 1), "decrease greater" should read --decrease (greater--.

Signed and Sealed this

Fourth Day of April, 1995

Attest:

BRUCE LEHMAN

Attesting Officer

Commissioner of Patents and Trademarks